(12) United States Patent
Shimoyama et al.

(10) Patent No.: US 9,504,417 B2
(45) Date of Patent: Nov. 29, 2016

(54) ORAL CAVITY SENSOR

(71) Applicants: The University of Tokyo, Toyko (JP); Meiji Co., Ltd., Tokyo (JP); Osaka University, Osaka (JP)

(72) Inventors: Isao Shimoyama, Tokyo (JP); Kiyoshi Matsumoto, Tokyo (JP); Yusuke Takei, Tokyo (JP); Kentaro Noda, Tokyo (JP); Yoshio Toyama, Kanagawa (JP); Toshihiro Ohmori, Kanagawa (JP); Takashi Tachimura, Osaka (JP)

(73) Assignees: THE UNIVERSITY OF TOKYO, Tokyo (JP); MEIJI CO., LTD., Tokyo (JP); OSAKA UNIVERSITY, Osaka (JP)

( * ) Notice: Subject to any disclaimer, the term of this patent is extended or adjusted under 35 U.S.C. 154(b) by 58 days.

(21) Appl. No.: 14/363,361

(22) PCT Filed: Dec. 7, 2012

(86) PCT No.: PCT/JP2012/081805
§ 371 (c)(1),
(2) Date: Jun. 6, 2014

(87) PCT Pub. No.: WO2013/085038
PCT Pub. Date: Jun. 13, 2013

(65) Prior Publication Data
US 2014/0343373 A1 Nov. 20, 2014

(30) Foreign Application Priority Data
Dec. 9, 2011 (JP) .................. 2011-270328

(51) Int. Cl.
*A61B 5/103* (2006.01)
*A61B 5/117* (2016.01)
(Continued)

(52) U.S. Cl.
CPC ............. *A61B 5/228* (2013.01); *A61B 5/01* (2013.01); *A61B 5/03* (2013.01); *A61B 5/1107* (2013.01); *A61B 5/682* (2013.01); *A61C 19/04* (2013.01); *A61B 2562/0247* (2013.01)

(58) Field of Classification Search
CPC ............................................. A61B 5/00
USPC ............................. 600/301, 587, 590
See application file for complete search history.

(56) References Cited

U.S. PATENT DOCUMENTS 4,629,424 A * 12/1986 Lauks ............... A61B 5/0002
257/417
4,697,601 A * 10/1987 Durkee ............... A61B 5/228
600/590

(Continued)

FOREIGN PATENT DOCUMENTS

JP     2006000234 A    1/2006
JP     2008 018094 A   1/2008

(Continued)

OTHER PUBLICATIONS

Extended European Search Report from corresponding Application No. PCT/JP2012/081805; Dated Jun. 15, 2015.

(Continued)

*Primary Examiner* — Rene Towo
*Assistant Examiner* — May Abouelela
(74) *Attorney, Agent, or Firm* — Pearne & Gordan LLP

(57) ABSTRACT

To propose an oral cavity sensor capable of analyzing tongue movements in more detail than before. In an oral cavity sensor (1) which is even provided with a sensor element (7) having a mechanical configuration capable of measuring each of external force components in three axis directions, the sensor element (7) can be protected by an elastic body (9), and the whole of the elastic body (9) is covered with the coating film (11*a*) made of a biocompatible material. Thereby, the sensor element (7) and the elastic body (9) can be safely attached in an oral cavity (MT) of a subject (EXA), and can measure each of the external force components in the three axis directions. As a result, on the basis of the external force components in the three axis directions, complicated tongue movements at the time of mastication or swallowing in the oral cavity (MT) can be analyzed in more detail than before.

6 Claims, 30 Drawing Sheets

(51) Int. Cl.
  *A61B 5/22* (2006.01)
  *A61B 5/03* (2006.01)
  *A61B 5/11* (2006.01)
  *A61B 5/00* (2006.01)
  *A61B 5/01* (2006.01)
  *A61C 19/04* (2006.01)

(56) References Cited

U.S. PATENT DOCUMENTS

| | | | | |
|---|---|---|---|---|
| 5,452,727 | A * | 9/1995 | Tura | A61B 5/228 128/860 |
| 6,190,335 | B1 * | 2/2001 | Howard | A61B 5/228 600/587 |
| 6,511,441 | B1 * | 1/2003 | Wakumoto | A61B 5/228 600/561 |
| 6,702,765 | B2 * | 3/2004 | Robbins | A61B 5/228 600/590 |
| 7,481,774 | B2 * | 1/2009 | Brockway | A61B 5/036 600/466 |
| 8,366,639 | B2 * | 2/2013 | Toyota | A61B 5/038 600/561 |
| 9,149,681 | B2 * | 10/2015 | Smead | A63B 21/02 |
| 2003/0078521 | A1 * | 4/2003 | Robbins | A61B 5/228 600/587 |
| 2003/0163065 | A1 * | 8/2003 | Nakao | A61B 5/228 600/590 |
| 2006/0030792 | A1 * | 2/2006 | Annest | A61B 5/1075 600/587 |
| 2007/0060847 | A1 * | 3/2007 | Leo | A61B 5/0084 600/587 |
| 2007/0188285 | A1 | 8/2007 | Shimoyama et al. | |
| 2008/0183107 | A1 * | 7/2008 | Miller | A61B 5/228 600/590 |
| 2009/0112263 | A1 * | 4/2009 | Pool | A61B 17/7016 606/246 |
| 2009/0186324 | A1 | 7/2009 | Penake et al. | |
| 2009/0309747 | A1 | 12/2009 | Ghovanloo et al. | |
| 2010/0222706 | A1 * | 9/2010 | Miyahara | A61B 5/038 600/590 |
| 2011/0190666 | A1 * | 8/2011 | Friedland | A61B 13/00 600/590 |
| 2012/0143091 | A1 * | 6/2012 | Annett | A61B 5/228 600/590 |
| 2013/0140289 | A1 * | 6/2013 | Baratier | A61C 7/36 219/121.83 |

FOREIGN PATENT DOCUMENTS

| | | |
|---|---|---|
| JP | 2010273840 A | 12/2010 |
| JP | 2011510349 A | 3/2011 |
| WO | 2008/039921 A2 | 4/2008 |
| WO | 2009/092107 A2 | 7/2009 |

OTHER PUBLICATIONS

International Search Report from PCT/JP2012/081805.

* cited by examiner

ORAL CAVITY SENSOR

TECHNICAL FIELD

The present invention relates to an oral cavity sensor and is suitably applied, for example, when tongue movements in masticating or swallowing are analyzed or when a food that can be easily swallowed is developed.

BACKGROUND ART

Currently, as a sensor used for analyzing tongue movements in the oral cavity in masticating and swallowing, there is known a tongue pressure sensor which is attached to a palate (the upper wall in the oral cavity) of a subject and which is configured to analyze tongue movements by measuring pressure at the time when the tongue comes into contact with a pressure-sensitive sensor arranged at a predetermined position of the palate (see, for example, Patent Literature 1). In practice, the tongue pressure sensor includes a base section attached to the palate, and a strip-like branch section branched from the base section and similarly attached to the palate, and has a configuration in which a plurality of pressure-sensitive sensors are provided at each of the base section and the branch section.

Here, the pressure-sensitive sensor used for the tongue pressure sensor is configured such that two pressure-sensitive ink layers are arranged so as to face each other via a predetermined gap, and such that, when a pressure is applied to the side of the palate by the tongue, the two pressure-sensitive ink layers are brought into contact with each other by this pressure so that electric resistance values (also referred to as a resistance value) of the two pressure-sensitive ink layers can be changed. Thereby, the analysis of tongue movements can be performed in such a manner that the tongue pressure sensor detects the pressure applied to each of the pressure-sensitive sensors and the position of the applied pressure by measuring a change of the electric resistance value of the pressure-sensitive ink layer of each of the pressure-sensitive sensors.

CITATION LIST

Patent Literature

Patent Literature 1: Japanese Patent Laid-Open No. 2010-273840

SUMMARY OF INVENTION

Technical Problem

However, in the tongue pressure sensor configured in this way, the external force, which can be measured by the pressure-sensitive sensor, is only the vertical pressure applied from the tongue to the side of palate in the oral cavity vertical direction. Therefore, movements of the tongue, which moves in front-rear, up-down, and left-right directions in a complicated manner, are difficult to be grasped in detail only on the basis of the vertical pressure applied in the oral cavity vertical direction, which results in a problem that the tongue movements cannot be sufficiently analyzed.

The present invention has been made in view of the above described circumstances. An object of the present invention is to propose an oral cavity sensor which enables tongue movements to be analyzed in more detail than before.

Solution to Problem

In order to solve the above described problem, an oral cavity sensor according to the present invention has a sensor main body attached in an oral cavity of a subject so as to measure external force applied from a tongue in the oral cavity, and is featured in that the sensor main body includes an elastic body elastically deformable by external force applied from the tongue, a sensor element embedded in the elastic body and configured, on the basis of a displacement state of the elastic body, to measure external force components in three axis directions orthogonal to each other, and a coating film made of a biocompatible material and covering the elastic body.

Advantageous Effects of Invention

In the oral cavity sensor of the present invention, which even includes the sensor element provided with a mechanical configuration capable of measuring each of the external force components in the three axis directions, the sensor element can be protected by the elastic body, and further, the elastic body is covered with the coating film made of the biocompatible material, whereby the sensor element and the elastic body can be safely attached in the oral cavity of the subject, so as to measure each of the external force components in the three axis directions. As a result, on the basis of the external force components in the three axis directions, complicated tongue movements at the time of mastication or swallowing in the oral cavity can be analyzed in more detail than before.

Figure 1:
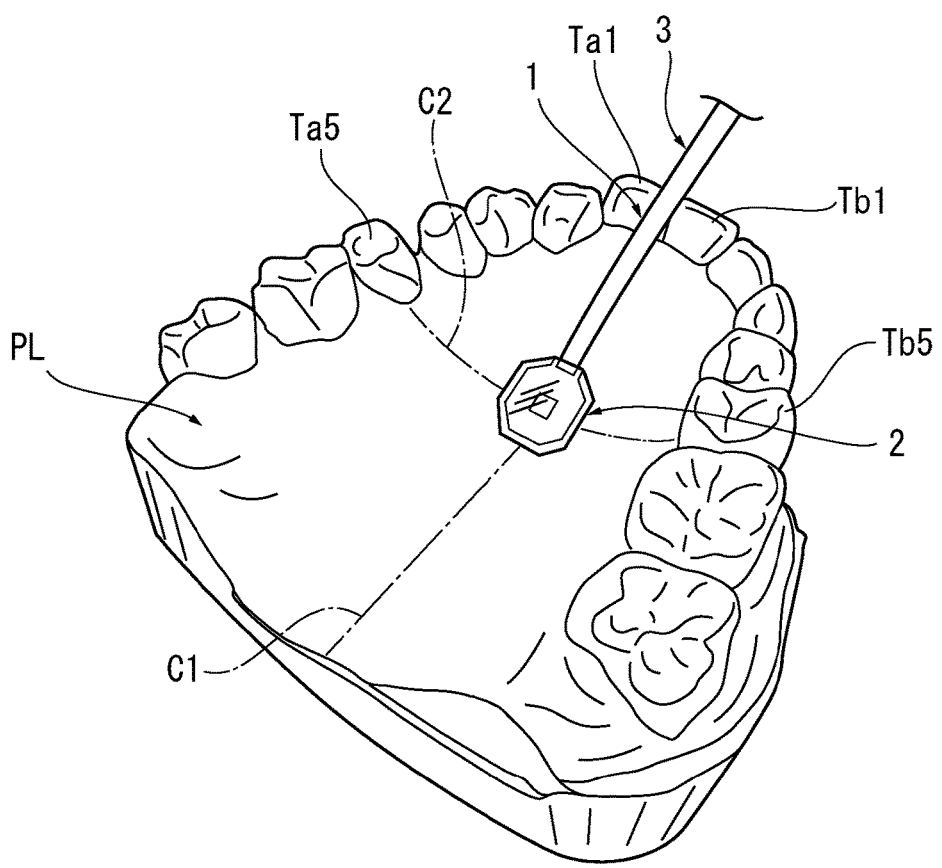
FIG. 1 is a schematic representation showing a state in which an oral cavity sensor is attached to a palate.

REFERENCE SIGNS LIST 1, 61 Oral cavity sensor
2 Sensor main body
3 Wiring body
7, 51 Sensor element
9 Elastic body
11a, 11b Coating film
21a First sensor section
21b Second sensor section
21c Third sensor section
62a First sensor main body (sensor main body)
62b Second sensor main body (sensor main body)

DESCRIPTION OF EMBODIMENTS

In the following, embodiments according to the present invention will be described with reference to the accompanying drawings.

(1) Outline of Oral Cavity Sensor

In FIG. 1, reference numeral 1 denotes an oral cavity sensor according to the present invention, which sensor is bonded at a predetermined position of a palate PL of a subject, and which is configured to be able to measure each of external force components in three axis directions, the external force components being applied to the palate PL by tongue movements in masticating or swallowing. Here, the external force components applied in the three axis directions represent a front-rear shearing stress which is applied in the oral cavity front-rear direction x in parallel with a raphe palati (a ridge line on a median line (line longitudinally passing through the center of a living body) of the palate PL) C1, a left-right shearing stress which is applied in the oral cavity left-right direction y which is perpendicular to the oral cavity front-rear direction x in the oral cavity and extending in the left and right direction with respect to the raphe palati C1, and a vertical pressure which is applied in the oral cavity vertical direction z perpendicular to the oral cavity front-rear direction x and the oral cavity left-right direction y.

In practice, the oral cavity sensor 1 includes a sensor main body 2 which can be brought into contact with the tongue (not shown) and which is bonded at a predetermined position in the oral cavity, and a wiring body 3 which is drawn out from the sensor main body 2. In the oral cavity sensor 1, the wiring body 3 can be drawn from the inside of the oral cavity to the outside of the oral cavity, so that the measurement results obtained from the sensor main body 2 can be sent out, via the wiring body 3, to a measurement apparatus (not shown) provided outside the oral cavity. Thereby, the measurement apparatus can display, on a display thereof, the measurement results obtained from the oral cavity sensor 1, so as to enable the movements of the tongue of the subject to be analyzed on the basis of the displayed measurement results.

Specifically, in the case of the present embodiment, the sensor main body 2 is bonded, for example, at a position at which the raphe palati C1 of the hard palate occupying two-thirds of the front portion of the palate PL crosses a virtual line C2 mutually connecting second premolars Ta5 and Tb5 and extending in the oral cavity left-right direction y. Thereby, the sensor main body 2 is arranged so that the tongue easily comes into contact with the entire surface of the sensor main body 2.

Further, in the case of the present embodiment, the wiring body 3 drawn out from the sensor main body 2 can be made to pass from the raphe palati C1 along the papilla incisiva (an elliptical protuberance located on the median line immediately behind upper central incisors (upper front teeth) Ta1 and Tb1 of the palate), so as to be able to be drawn from the upper central incisors (upper front teeth) Ta1 and Tb1 to the outside of the oral cavity. It should be noted that the sensor main body 2 and the wiring body 3 are bonded on the palate PL by a medical adhesive, such as, for example, a denture stabilizer (product name "Touch Correct II", Shionogi & Co., Ltd.) so that, even when the subject masticates or swallows food, the bonded state of the sensor main body 2 and the wiring body 3 can be maintained without the sensor main body 2 and the wiring body 3 being separated and shifted from the palate PL.

Figure 2:
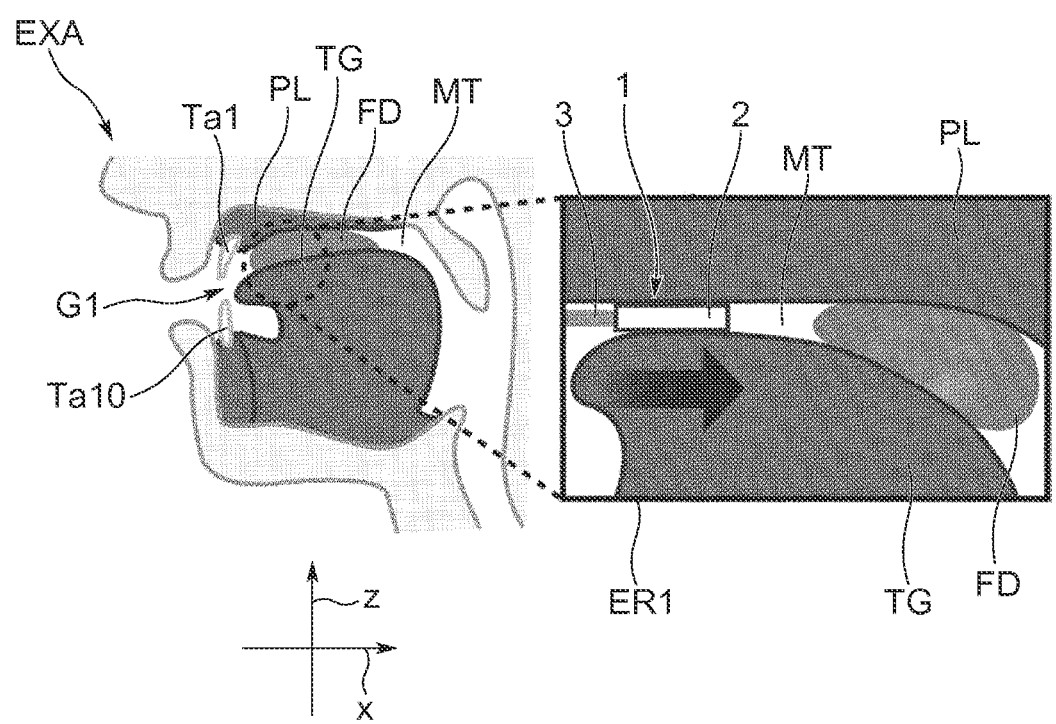
FIG. 2 is a schematic representation showing a state when a subject swallows food.

As shown in FIG. 2, the oral cavity sensor 1 is configured such that the sensor main body 2 is bonded on the palate PL (in this case, the hard palate) in the oral cavity MT, and such that, when the subject EXA masticates or swallows food FD, the food FD and the tongue TG can be brought into contact with the surface of the sensor main body 2, and thereby external forces given from the food FD and the tongue TG can be measured. It should be noted that the frame ER1 in FIG. 2 is a partially enlarged view of the inside of the oral cavity MT of the subject EXA.

Here, in practice, the oral cavity sensor 1 is configured such that each of a front-rear shearing stress in the oral cavity front-rear direction x, a left-right shearing stress in the oral cavity left-right direction y, and a vertical pressure in the oral cavity vertical direction z can be individually measured by the sensor main body 2. Thereby, the external force applied from the food FD and the tongue TG moving in a complicated manner at the time of mastication or swallowing is decomposed into the external force components in the three axis directions, so that, from each of the measurement results in the three axis directions, the movement of the tongue TG at the time of mastication or swallowing can be analyzed in more detail than before. It should be noted that the oral cavity sensor 1 is configured such that the wiring body 3 is made to pass through a gap G1 between the upper central incisor Ta1 and a lower central incisor (lower front tooth) Ta10 so as to be drawn out to the outside of the oral cavity MT.

Figure 3:
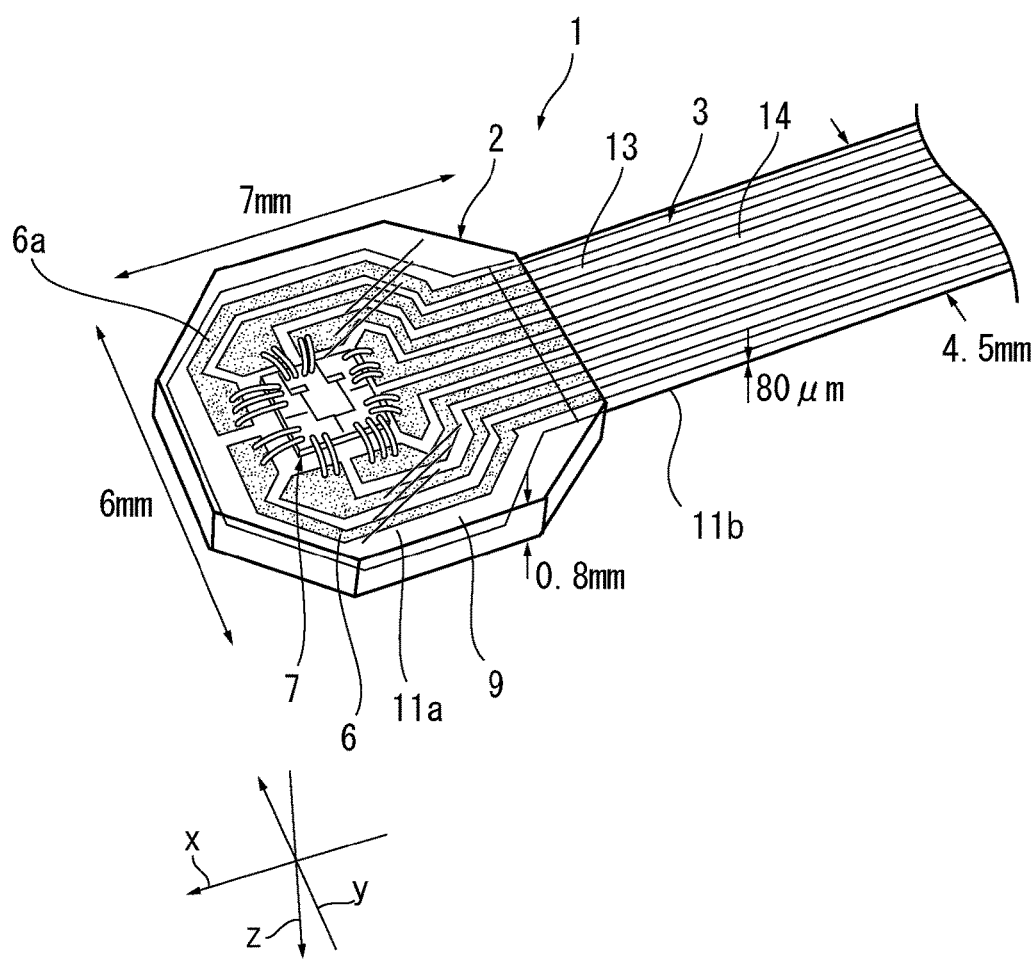
FIG. 3 is a schematic representation showing an entire configuration of the oral cavity sensor.

In the case of the present embodiment, as shown in FIG. 3, the oral cavity sensor 1 is configured such that the sensor main body 2 is formed, for example, in a flat shape having a width of 6 [mm], a depth of 7 [mm], and a thickness of 0.8 [mm], and is also formed to have an octagonal outline shape with rounded corners. Further, the sensor main body 2 includes a plate-like main-body-side flexible substrate 6, and a sensor element 7 provided on the flat sensor installation surface of the main-body-side flexible substrate 6. The main-body-side flexible substrates 6 and the sensor element 7 as a whole are covered with an elastic body 9 made of silicone rubber.

Further, the sensor main body 2 is configured such that, in addition to the flat-shaped elastic body 9, a coating film 11a, which is made of, for example, para-xylene based polymer (also referred to as parylene), such as parylene N, parylene C, and parylene HT (manufactured by Japan Parylene Co., Ltd.), is formed on the whole surface of the elastic body 9, and hence the coating film 11a prevents the elastic body 9 from being exposed to the outside. The sensor main body 2 can be arranged so that the flat coating film 11a on the one side serves as a bonding surface so as to be bonded to the palate PL in the oral cavity MT, and the flat coating film 11a on the other side serves as a contact surface so as to face the tongue TG.

It should be noted that, in the above-described embodiment, a case where the coating film 11a covering the elastic body 9 is formed of parylene is described, but the present invention is not limited to this. The coating film 11a may be formed by various biocompatible members, as long as each of the members is made of a biocompatible material which can seal the elastic body 9 and which can be applied to a living body without exhibiting toxicity to living tissues and cells, and without causing inflammatory reaction, and the like.

In the case of the present embodiment, the main-body-side flexible substrate 6 is formed to have an outline shape (octagonal shape in this case) the same as the outline shape of the sensor main body 2. Further, the sensor element 7 is installed at the center of a sensor installation surface of the main-body-side flexible substrate 6, and a wiring area section 6a, which has a predetermined shape and which is electrically connected to the sensor element 7, is formed around the sensor element 7. Here, the sensor element 7 is electrically connected to the wiring area section 6a by wires, so that electric signals from the sensor element 7 can be sent out to the wiring area section 6a.

The wiring body 3 formed integrally with the sensor main body 2 includes a strip-shaped wiring-side flexible substrate 13 formed integrally with the main-body-side flexible substrate 6 of the sensor main body 2, and the whole surface of the wiring-side flexible substrate 13 has a configuration covered with a coating film 11b made of parylene. Wirings 14 connected to the wiring area section 6a of the main-body-side flexible substrate 6 are formed in the wiring-side flexible substrate 13.

Thereby, the oral cavity sensor 1 is configured such that electric signals from the sensor element 7 are sent out to the wirings 14 of the wiring-side flexible substrate 13 via the wiring area section 6a of the main-body-side flexible substrate 6, and further the electric signals are sent out from the wirings 14 of the wiring body 3 to the measurement apparatus (not shown). In this way, the measurement results obtained from the oral cavity sensor 1 are visually displayed on the display of the measurement apparatus, so that tongue movements at the time of mastication or swallowing by the subject EXA can be analyzed on the basis of the visually displayed measurement results.

(2) Detailed Configuration of Sensor Main Body

Figure 4:
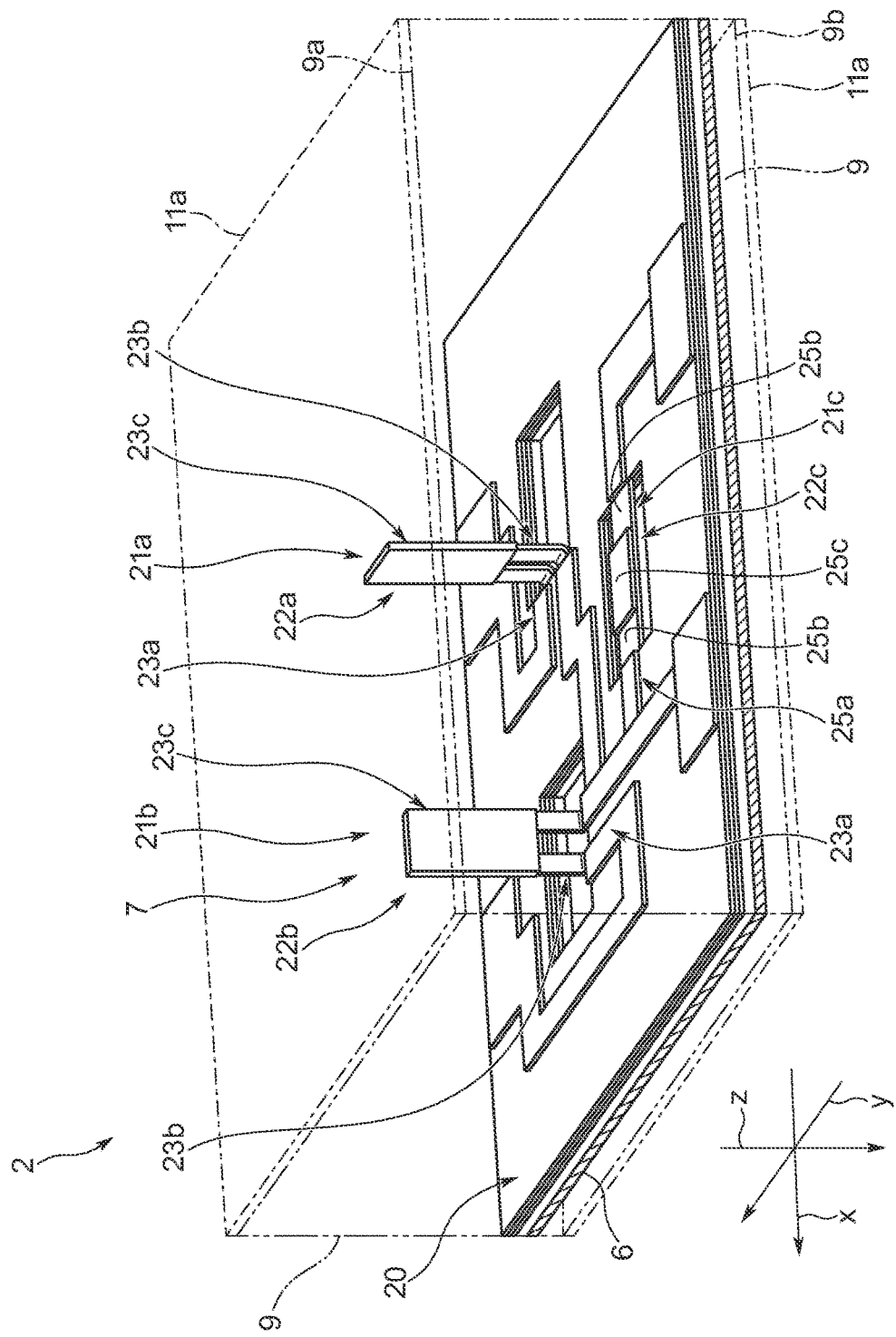
FIG. 4 is a schematic representation showing a detailed configuration of a sensor body.

Next, a detailed configuration of the sensor main body 2 will be described below. As shown in FIG. 4, the sensor main body 2 has a configuration in which the sensor element 7 is embedded in the elastic body 9, and further in which the elastic body 9 is covered with the coating film 11a. Here, the elastic body 9 is not only formed on the side of the sensor installation surface of the main-body-side flexible substrate 6 but also formed so as to cover the entire back surface of the sensor installation surface. A tongue facing surface 9a, that is, the surface facing the tongue TG, which is arranged on the side of the sensor installation surface of the main-body-side flexible substrate 6, is flatly formed. Thereby, the coating film 11a, which is a contact surface formed on the tongue facing surface 9a, is also flatly formed along the tongue facing surface 9a so that, when the tongue TG of the subject EXA comes into contact with the coating film 11a, the subject EXA can perform natural mastication or swallowing without having an excessive uneven feeling on the tongue TG and in a state in which uncomfortable feeling due to the presence of the sensor main body 2 on the palate PL is reduced.

Further, a palate facing surface 9b of the elastic body 9 on the back surface side of the main-body-side flexible substrate 6, that is, the surface of the elastic body 9 on the side bonded to the palate PL is also flatly formed. Thereby, the coating film 11a, serving as a bonding surface formed on the palate facing surface 9b, is also flatly formed along the palate facing surface 9b. Here, the elastic body 9 is formed of silicone rubber and has elasticity. Therefore, when the sensor main body 2 is bonded to the uneven palate PL with a medical adhesive, the palate facing surface 9b can be deformed along the uneven shape of the palate PL, so as to enable the sensor main body 2 to be bonded to the palate PL in a state in which the coating film 11a of the palate facing surface 9b is brought into close contact with the palate PL.

Thereby, when the subject EXA masticates or swallows food FD, the sensor main body 2 makes it difficult for the food FD to enter between the palate PL and the sensor main body 2. Further, the palate facing surface 9b is also displaced in association with a slight change of the palate PL at the time of mastication or swallowing, and hence the coating film 11a of the palate facing surface 9b can continue to be bonded to the palate PL. In this way, with the oral cavity sensor 1, when the subject EXA masticates or swallows food FD, the subject EXA can perform mastication or swallowing without worrying that the sensor main body 2 falls off. Therefore, the oral cavity sensor 1 can realize natural tongue movements the same as the movements as the time when the oral cavity sensor 1 is not arranged. Thereby, it is possible to obtain measurement results of natural tongue movements at the time of mastication or swallowing.

Here, the sensor element 7 arranged in the elastic body 9 is configured to be able to measure each of external force components in the three axis directions orthogonal to each other, that is, to measure the front-rear shearing stress in the oral cavity front-rear direction x, the left-right shearing stress in the oral cavity left-right direction y, and the vertical pressure in the oral cavity vertical direction z. In practice, in the sensor element 7, a first sensor section 21a configured to measure the front-rear shearing stress acting in the oral cavity front-rear direction (first direction) x, a second sensor section 21b configured to measure the left-right shearing stress acting in the oral cavity left-right direction (second direction) y, and a third sensor section 21c configured to measure the vertical pressure acting in the oral cavity vertical direction (third direction) z are formed in a base section 20 at predetermined intervals from each other.

The first sensor section 21a and the second sensor section 21b are respectively provided with cantilever-shaped cantilever sections 22a and 22b, and are formed such that one end side of each of the cantilever sections 22a and 22b is fixed to the base section 20, and such that the other end side of each of the cantilever sections 22a and 22b is erected on the base section 20.

In practice, each of the cantilever sections 22a and 22b is configured by a base 23a provided at the one end and fixed to the base section 20, a pair of L-shaped hinge sections 23b connected to the base 23a, and a plate-shaped movable section 23c provided at the other end and connected to the hinge section 23b. When no external force is applied, each of the cantilever sections 22a and 22b can be held in a state where the movable section 23c is erected substantially vertically to the base section 20 by the bent hinge section 23b.

Here, in the sensor main body 2, for example, when an external force is applied, by the tongue TG, to the coating film 11a serving as the contact surface, the elastic body 9 can be displaced according to the external force, and each of the movable sections 23c of the cantilever sections 22a and 22b can receive the external force from the elastic body 9, so that the movable section 23c is tilted around the hinge section 23b. In this case, each of the cantilever sections 22a and 22b is configured such that each of the hinge sections 23b functions as a piezoelectric element to measure, as a resistance value change, the displacement of the movable section 23c.

In practice, in the first sensor section 21a, the surface portion of the plate-shaped movable section 23c is arranged vertically to the oral cavity front-rear direction x, so that the movable section 23c can receive the front-rear shearing stress applied in the oral cavity front-rear direction x. Thereby, in the first sensor section 21a, the movable section 23c can be made to tilt in the oral cavity front-rear direction x. In the first sensor section 21a, when the hinge section 23b is deformed by an external force, the crystal lattice of the hinge section 23b is distorted, and thereby the amount and mobility of carriers of the semiconductor can be changed, so that the resistance value of the semiconductor can be changed. Thereby, in the first sensor section 21a, a resistance value change is given between end point electrodes of the hinge sections 23b having the two-leg structure, so that the front-rear shearing stress applied to the cantilever section 22a can be measured from the result of measurement of the resistance value change.

On the other hand, in the second sensor section 21b, unlike the first sensor section 21a, the surface portion of the plate-shaped movable section 23c is arranged vertically to the oral cavity left-right direction y, so that the movable section 23c can receive the left-right shearing stress applied in the oral cavity left-right direction y. Thereby, in the second sensor section 21b, the movable section 23c can be made to tilt in the oral cavity left-right direction y. Further, similarly to the first sensor section 21a, also in the second sensor section 21b, a resistance value change is given between end point electrodes of the hinge sections 23b having the two-leg structure, so that the left-right shearing stress applied to the cantilever section 22b can be measured from the result of measurement of the resistance value change.

On the other hand, in the third sensor section 21c, unlike the first sensor section 21a and the second sensor section 21b, the surface of a plate-shaped movable section 25c is provided with a cantilever section 22c which has a both-end supported beam-shape and which is provided to be substantially flush with the base section 20. In the cantilever section 22c, a thin plate-shaped hinge section 25b formed to be flush with the base section 20 is provided at each of both ends of the movable section 25c. Thereby, when a vertical pressure is applied to the sensor main body 2 in the oral cavity vertical direction z, the vertical pressure applied from the deformed elastic body 9 can be received by the movable section 25c. Thereby, in the third sensor section 21c, the movable section 25c can be recessed and displaced to the side of the oral cavity vertical direction z. In the third sensor section 21c, a resistance value change is given between end point electrodes of the hinge section 25b, so that the vertical pressure applied to the cantilever section 22c in the oral cavity vertical direction z can be measured from the result of measurement of the resistance value change.

In this way, in each of the first sensor section 21a, the second sensor section 21b, and the third sensor section 21c, when an external force is applied from the elastic body 9, each of the movable sections 23c and 25c corresponding to the applied direction of the external force receives the external force, so as to enable each of the hinge sections 23b and 25b to be displaced. Thereby, the sensor element 7 can measure the deformation of each of the hinge sections 23b and 25b as a resistance value change, so that the external force given by the tongue movements can be specified as three axis direction external force components of the front-rear shearing stress, the left-right shearing stress, and the vertical pressure.

Figure 5:
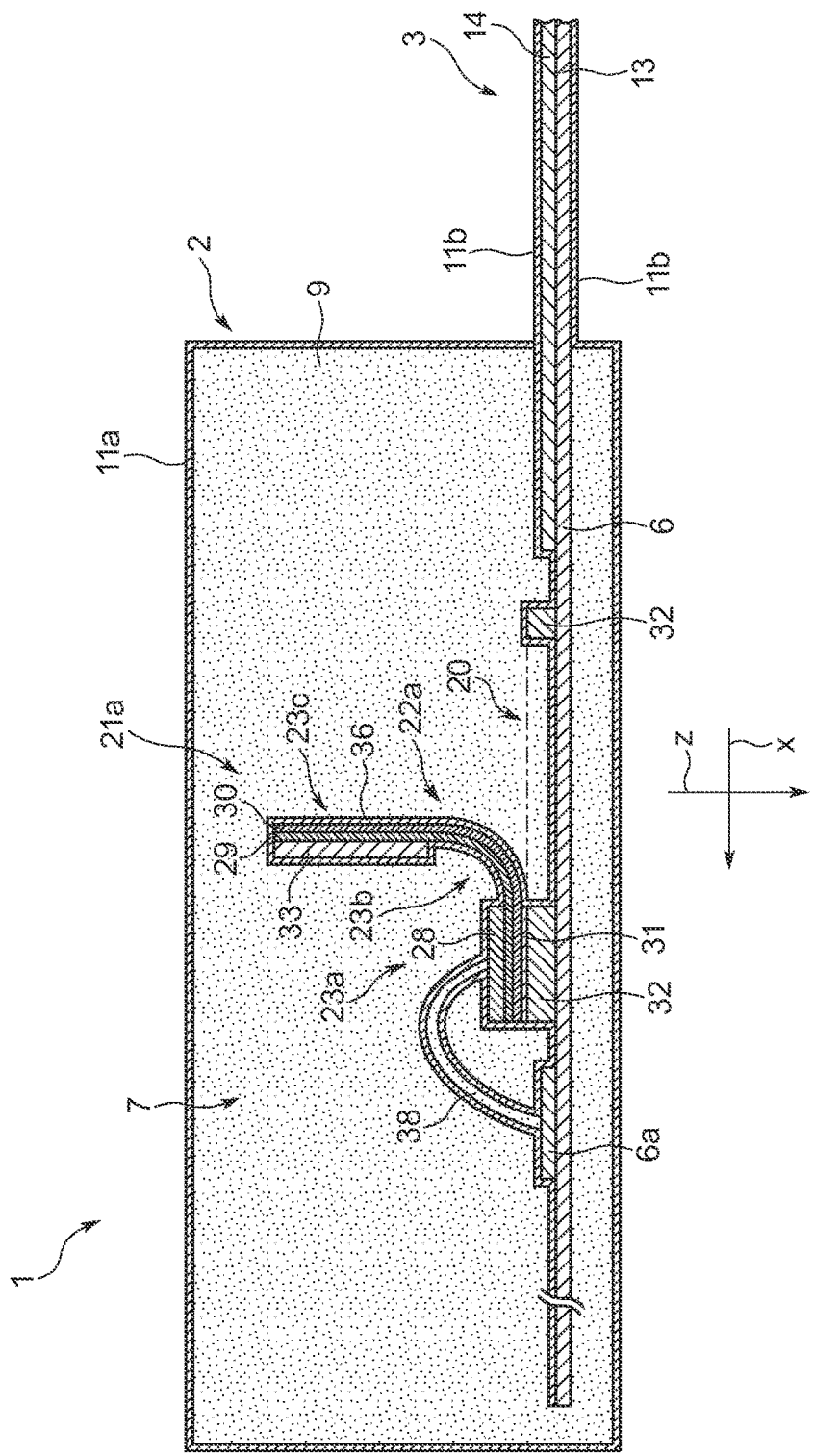
FIG. 5 is a schematic representation showing a cross-sectional configuration of the oral cavity sensor.

It should be noted that the first sensor section 21a and the second sensor section 21b are different from each other only in the installation direction of the movable section 23c, and the other configurations of the first sensor section 21a and the second sensor section 21b are the same as each other. Hence, in the following, the detailed description of the configuration will be made mainly focusing on the configuration of the first sensor section 21a. FIG. 5 is a schematic representation showing a side cross-sectional configuration of the oral cavity sensor 1 focusing on the first sensor section 21a and omitting the other sensor sections of the second sensor section 21b and the third sensor section 21c.

As shown in FIG. 5, the cantilever section 22a of the first sensor section 21a has an L-shaped Si upper layer 30 formed by an Si thin film. A thin-film piezoresistive layer 29 is formed on the surface of the Si upper layer 30, and Au/Ni thin films 28 and 33 are formed on the piezoresistive layer 29 formed in the base 23a and the movable section 23c. It should be noted that an Si lower layer 32 is provided in the base section 20, and the base 23a of the cantilever section 22a is provided at a predetermined position of the Si lower layer 32 via an $SiO_2$ layer 31.

In the cantilever section 22a, the Si upper layer 30 and the piezoresistive layer 29 of the hinge section 23b are formed in a state of a thin film of nm order thickness, and a piezoresistive layer 29 of the hinge section 23b can function as a piezoelectric element. Here, in the case of the present embodiment, the cantilever section 22a is configured such that, except the hinge section 23b, the base 23a and the movable section 23c are respectively covered by the Au/Ni thin films 28 and 33, so that the resistance value corresponding to the deformation of the hinge section 23b can be measured. That is, the cantilever section 22a is configured such that, when the hinge section 23b is deformed by an external force, the crystal lattice of the hinge section 23b is distorted to change the amount and mobility of carriers of the semiconductor, so that the resistance value of the semiconductor can be changed and thereby the front-rear shearing stress can be measured on the basis of the resistance value change of the hinge section 23b.

It should be noted that, in the cantilever section 22a, one end of a wire 38 is electrically connected to the Au/Ni thin film 28 provided in the base 23a. The other end of the wire 38 is connected to the wiring area section 6a of the main-body-side flexible substrate 6, so as to be able to send out, to the wiring area section 6a, an electric signal representing the resistance value change in the hinge section 23b as a measurement result.

Further, in the sensor element 7, in addition to the base section 20, the main-body-side flexible substrate 6, the wire 38, the first sensor section 21a on the base section 20, the second sensor section 21b and the third sensor section 21c (not shown, refer to FIG. 4) are all covered with a protective film 36 made of parylene. The protective film 36 is formed to have a thickness of about 1 [μm] and to provide a mechanical strength to the hinge section 23b so that, for example, the erecting state of the movable section 23c in the cantilever section 22a can be maintained. The protective film 36 is also formed so that, when the elastic body 9 is displaced, the hinge section 23b is bent according to the displacement so as to allow the movable section 23c to be tilted.

It should be noted that, in the wiring body 3, one surface and the other surface of the wiring-side flexible substrate 13, and the wiring 14 of the wiring-side flexible substrate 13 are all covered with the coating film 11b, and the connecting portion between the wiring body 3 and the sensor main body 2 is also covered with the coating film 11b. In this way, the oral cavity sensor 1 has a structure in which not only the sensor main body 2 attached in the oral cavity MT of the subject EXA but also the wiring body 3 attached in the oral cavity MT are all covered with the coating film 11b made of parylene applicable to a living body.

(3) Manufacturing Method of Sensor Element and Oral Cavity Sensor

Figure 6A:
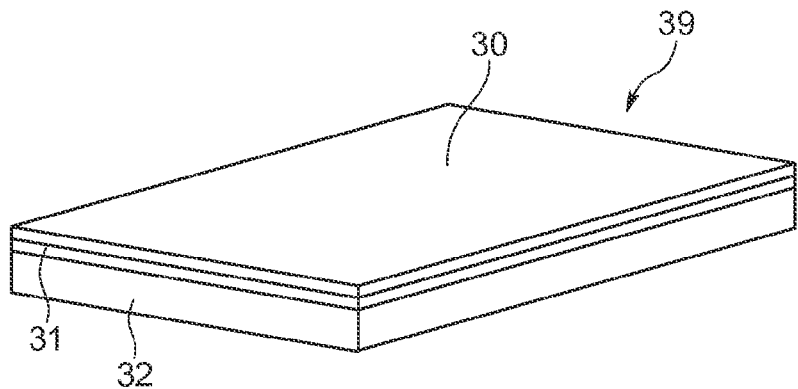
FIG. 6A is a schematic representation for explaining a manufacturing method of the sensor body.
Figure 6B:
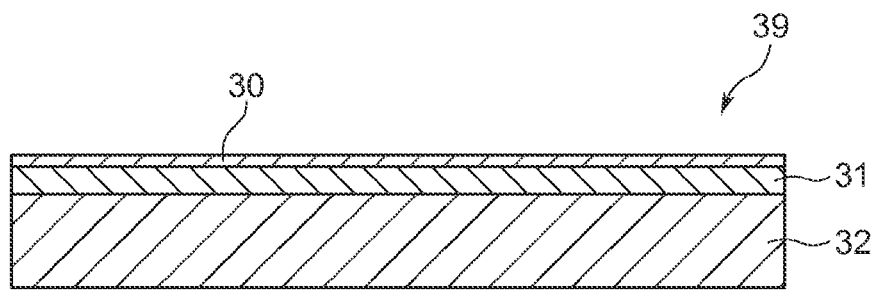
FIG. 6B is a schematic representation for explaining a manufacturing method of the sensor body.

Next, there will be described a method for manufacturing the above-described sensor element 7, and the oral cavity sensor 1 provided with the sensor element 7. It should be noted that the manufacturing methods of the first sensor section 21a, the second sensor section 21b, and the third sensor section 21c of the sensor element 7 are substantially the same, and hence, the description will be given focusing on the first sensor section 21a. First, as shown in FIG. 6A and FIG. 6B, an SOI (Silicon On Insulator) substrate 39 is prepared, in which the Si upper layer 30, the $SiO_2$ layer 31, and the Si lower layer 32 are laminated in order from the surface of the SOI substrate 39. It should be noted that the SOI substrate 39 is washed in an HF (hydrogen fluoride) solution to remove a natural oxide film formed on the surface of the SOI substrate 39.

Figure 7A:
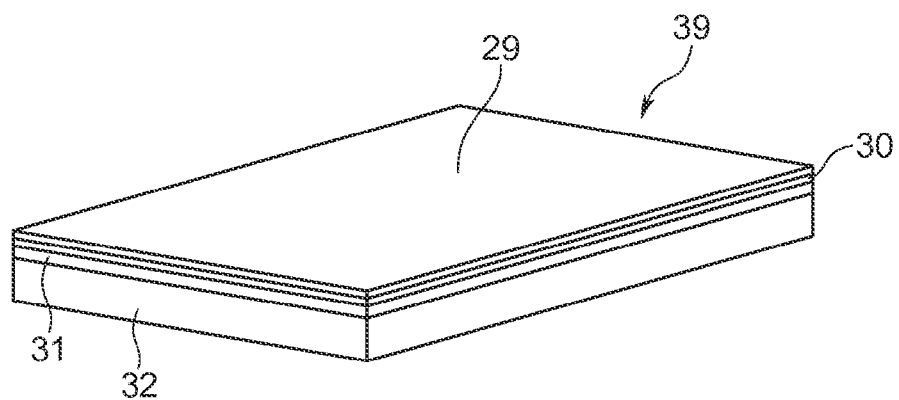
FIG. 7A is a schematic representation for explaining the manufacturing method of the sensor body.
Figure 7B:
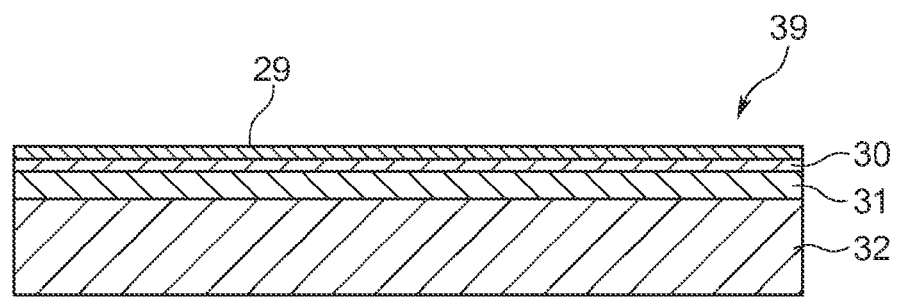
FIG. 7B is a schematic representation for explaining a manufacturing method of the sensor body.
Figure 8A:
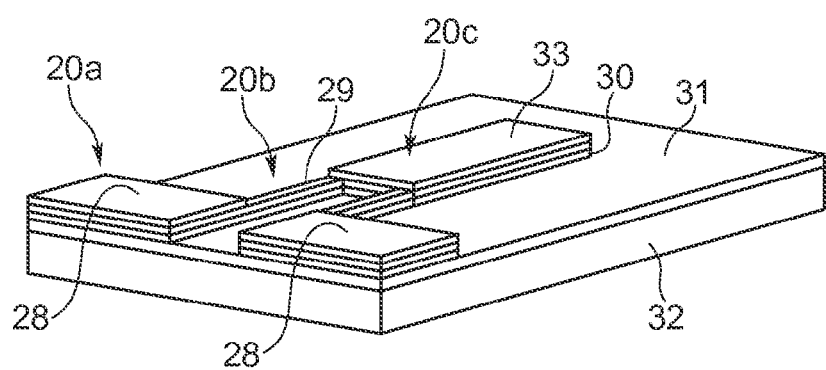
FIG. 8A is a schematic representation for explaining the manufacturing method of the sensor body.
Figure 8B:
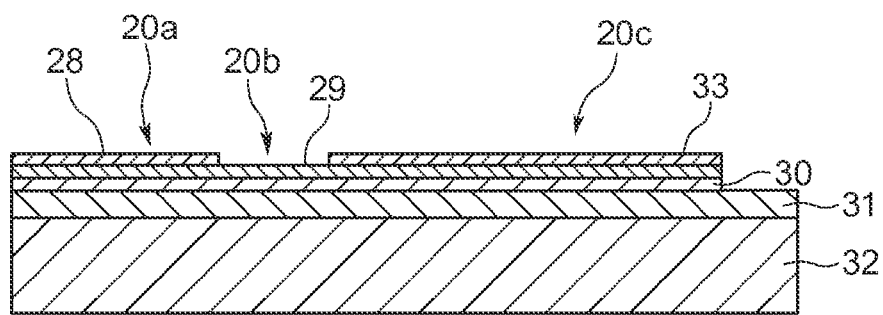
FIG. 8B is a schematic representation for explaining a manufacturing method of the sensor body.

Then, as shown in FIG. 7A and FIG. 7B, the piezoresistive layer 29 is immediately formed on the Si upper layer 30 in such a manner that an n-type impurity material P-59230 (OCD, Tokyo Ohka Kogyo Co., Ltd.) is spin coated on the surface of the SOI substrate 39, and then thermal diffusion is performed in the SOI substrate 39 by using a thermal oxidation furnace, so that impurities are doped in a thickness of 100 [nm] or less. Then, an Au/Ni layer is formed on the surface of the piezoresistive layer 29 of the SOI substrate 39 by sputtering and is then patterned in a predetermined shape. Then, the piezoresistive layer 29 and the Si upper layer 30 are etched by DRIE (Deep Reactive Ion Etching) using the Au/Ni layer as a mask. Thereby, the SOI substrate 39 can be formed, as shown in FIG. 8A and FIG. 8B, such that the Au/Ni thin film 28 is formed in a base formation region 20a which is to be formed as the base 23a in the subsequent process, such that the piezoresistive layer 29 is exposed to a hinge section formation region 20b which is to be formed as the hinge section 23b in the subsequent process, and such that the Au/Ni thin film 33 is formed in the movable section region 20c which is to be formed as the movable section 23c in the subsequent process.

Figure 9A:
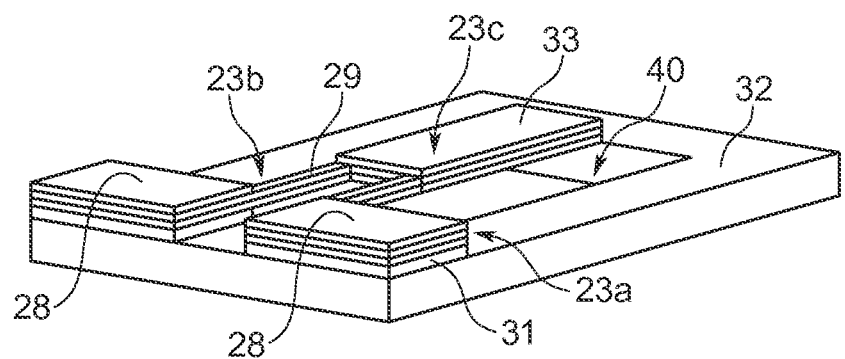
FIG. 9A is a schematic representation for explaining the manufacturing method of the sensor body.
Figure 9B:
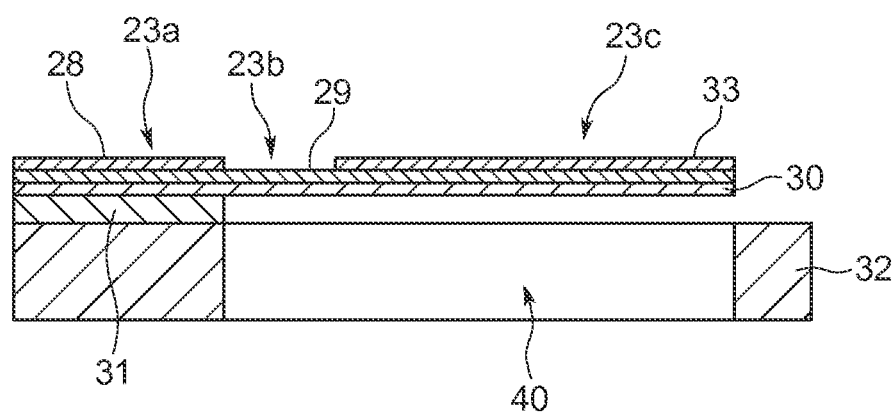
FIG. 9B is a schematic representation for explaining a manufacturing method of the sensor body.

Next, the Si lower layer 32 located directly under the hinge section formation region 20b and the movable section region 20c is etched by DRIE so as to leave the base formation region 20a, and further the $SiO_2$ layer 31 is removed by HF (hydrogen fluoride). Thereby, as shown in FIG. 9A and FIG. 9B, the hinge section 23b, and the movable section 23c serving as a free end are formed in an opening region 40 of the Si lower layer 32, so that a sensor element member is manufactured.

Figure 10:
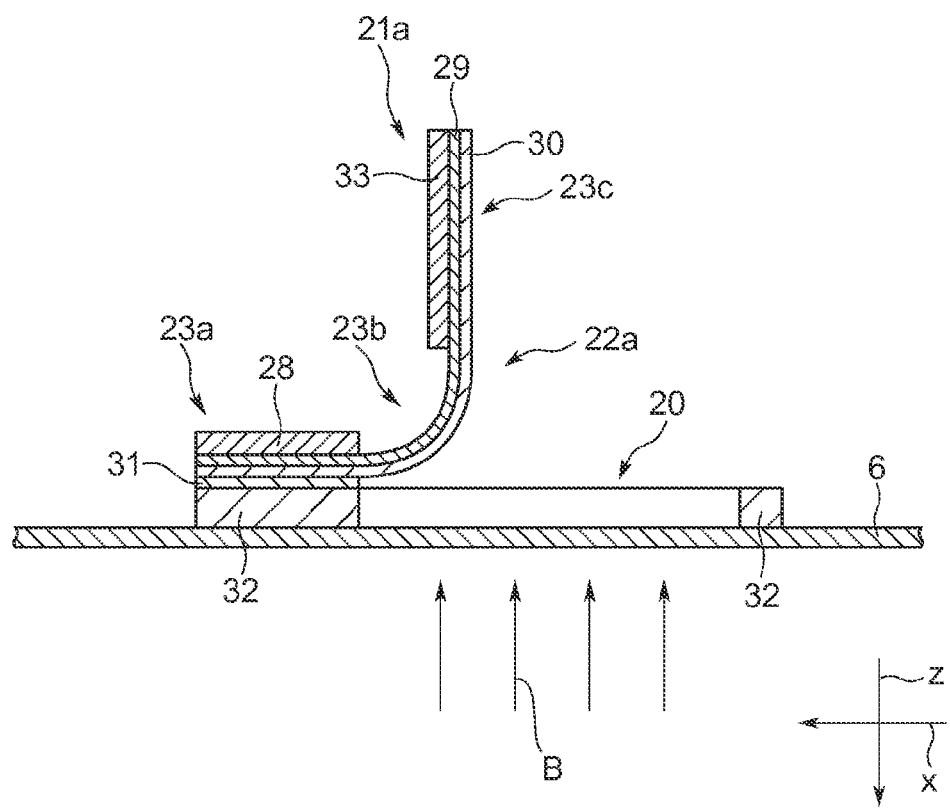
FIG. 10 is a schematic representation for explaining a case where a movable section of a cantilever section is erected.

Then, apart from this, the main-body-side flexible substrate 6 integrally formed with the wiring-side flexible substrate 13 (FIG. 3) is prepared. Then, as shown in FIG. 10, the sensor element member described above is fixed, with an adhesive, at a predetermined position of the one surface of the main-body-side flexible substrate 6. Thereafter, a magnetic field along the oral cavity vertical direction z (the arrow direction B in FIG. 10) is applied from under the main-body-side flexible substrate 6, so that the movable section 23c, which is a free end having the Au/Ni thin film 33, can be displaced in the oral cavity vertical direction z by the magnetic field. Thereby, the hinge section 23b is bent, and the movable section 23c is erected, so that the cantilever section 22a is formed in a state where the surface portion of the movable section 23c is vertically arranged with respect to the oral cavity front-rear direction x. As a result, the sensor element 7 can be manufactured.

It should be noted that the magnetic field is applied by using a neodymium magnet (NE009, Niroku Seisakusho Co., Ltd.). It should be noted that the second sensor section 21b shown in FIG. 4 is different from the first sensor section 21a only in the direction of the hinge section 23b and the movable section 23c, and is manufactured by the same method as the manufacturing method of the first sensor section 21a described above. Therefore, the description of the manufacturing method of the second sensor section 21b is omitted here. Further, the third sensor section 21c shown in FIG. 4 is the same as the first sensor section 21a described above except that the movable section 25c and the hinge sections 25b are formed in a both-end supported beam shape, and that the movable section 25c is not erected in the manufacturing process. Therefore, the third sensor section 21c can be manufactured according to the manufacturing method of the first sensor section 21a described above, and hence the description of the manufacturing method of the third sensor section 21c is omitted here.

Figure 11:
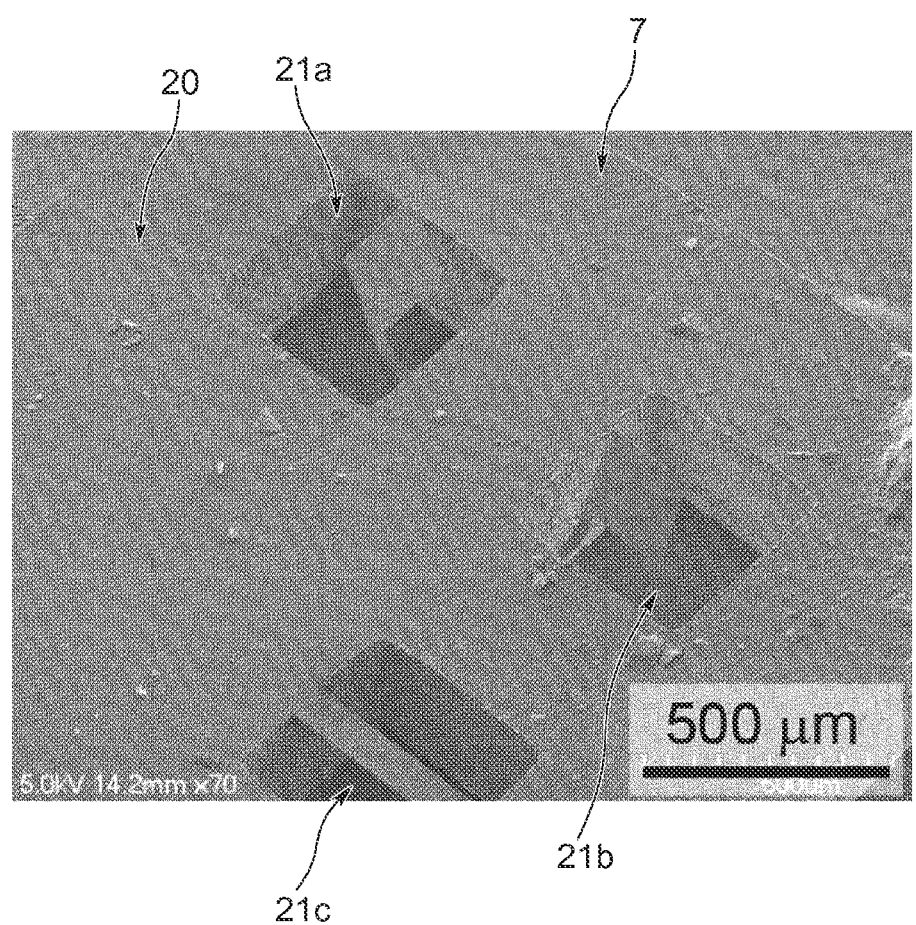
FIG. 11 is an SEM image showing a configuration of a sensor element.

Next, as shown in FIG. 5, the Au/Ni thin film 28 provided as an electrode in the base section 20 of the sensor element 7, and the wiring area section 6a on the main-body-side flexible substrate 6 are connected to each other by the wire 38, and then the protective film 36 having a thickness of 1 [μm] and made of parylene is formed, by a chemical vapor deposition method (CVD method), on the whole of the main-body-side flexible substrate 6, the wire 38, and the sensor element 7. Thereby, the erected state of the movable section 23c can be maintained by the protective film 36. It should be noted that FIG. 11 is an SEM image of the sensor element 7 manufactured by the manufacturing method described above. From the image, it can be confirmed that the first sensor section 21a and the second sensor section 21b are each bent in an L-shape and vertically erected with respect to the base section 20, and that the third sensor section 21c is formed in a beam shape.

Subsequently, the flat-shaped elastic body 9 is formed so as to cover the whole of the main-body-side flexible substrate 6 provided with the sensor element 7, so that the elastic body 9 prevents the main-body-side flexible substrate 6 from being exposed to the outside. At this time, each of the tongue facing surface 9a and the palate facing surface 9b of the elastic body 9 can be flatly formed. Further, here, Polydimethylsiloxane (PDMS: SILPOT184 manufactured by Dow Corning Toray Co., Ltd.) is used as the elastic material forming the elastic body 9.

In practice, the elastic body 9 is manufactured as follows. First, a base material of PDMS and a hardener are mixed with each other at a predetermined ratio, so as to prepare an elastic material for forming the elastic body 9. It should be noted that, as the elastic member, it is preferred to use an elastic member having a weight ratio between the base material and the hardener of, for example, 10:1, in order to realize the hardness with which, in the case where the sensor main body 2 is bonded to the palate PL of the subject EXA to analyze tongue movements, the elastic body 9 is not damaged even when the tongue TG and food FD come into contact with the sensor main body 2 in the oral cavity MT, and in order to realize the softness with which the elastic body 9 can be flexibly deformed by receiving an external force from the tongue TG or the food FD.

Next, the prepared PDMS as the elastic material is stirred by using a centrifugal degassing apparatus (THINKY MIXER ARE-250, Thinky Co., Ltd.), and is degassed in a desiccator. Further, apart from this, a box body (not shown), in the inner space of which the outline shape of the sensor main body 2 is formed, and one surface of which is opened, is prepared. The main-body-side flexible substrate 6 provided with the sensor element 7 is positioned in the inner space of the box body from the opening of the box body so as not to be in contact with the inner wall of the box body. Then, the PDMS as the elastic material is poured into the inner space from the opening of the box body, and the box body is again placed in the desiccator, and the degassing is performed. Thereafter, the PDMS as the elastic member is cured by being baked for 40 minutes in an oven kept at about 70[° C.], so as to be formed as the elastic body 9, and the formed elastic body 9 is taken out from the box body. In this manner, the elastic body 9 is formed in a flat shape, and the main-body-side flexible substrate 6 can be arranged in the elastic body 9. It should be noted that, in order that, when the elastic material is baked, the elastic body 9 to be formed is cured to have a flat surface shape, the box body is rotated by 90 degrees every five minutes, so as to prevent that the surface of the elastic body is inclined due to the inclination of the floor of the oven.

Finally, the coating film 11a having a thickness of 1 [μm] and made of parylene is formed, by the CVD method, on the whole surfaces of the outer surface of the elastic body 9 formed in the flat shape, and the surface of the wiring-side flexible substrate 13 drawn out from the elastic body 9. Thereby, the oral cavity sensor 1 as shown in FIG. 3 can be manufactured.

(4) Sensor Element when External Force is Applied to Sensor Main Body Attached to Palate Next, in the following, there will be described how, when an external force is applied from the tongue TG or food FD to the sensor main body 2 attached to the palate PL, the first sensor section 21a, the second sensor section 21b, and the third sensor section 21c of the sensor element 7 measure the external force components in the three axis directions. Here, when the tongue TG or food FD is not in contact with the sensor main body 2, and when no external force is applied to the sensor main body 2, the elastic body 9 of the sensor main body 2 is not displaced as shown in FIG. 12.

Thereby, in the sensor element 7, each of the cantilever sections 22a and 22b of the first sensor section 21a and the second sensor section 21b can maintain the erected state, and the cantilever section 22c of the third sensor section 21c can be maintained flush with the surface of the base section 20. Therefore, in the sensor element 7, the resistance value in each of the first sensor section 21a, the second sensor section 21b, and the third sensor section 21c is not changed, and the initial resistance values are continuously measured by a measurement apparatus (not shown).

Figure 12:
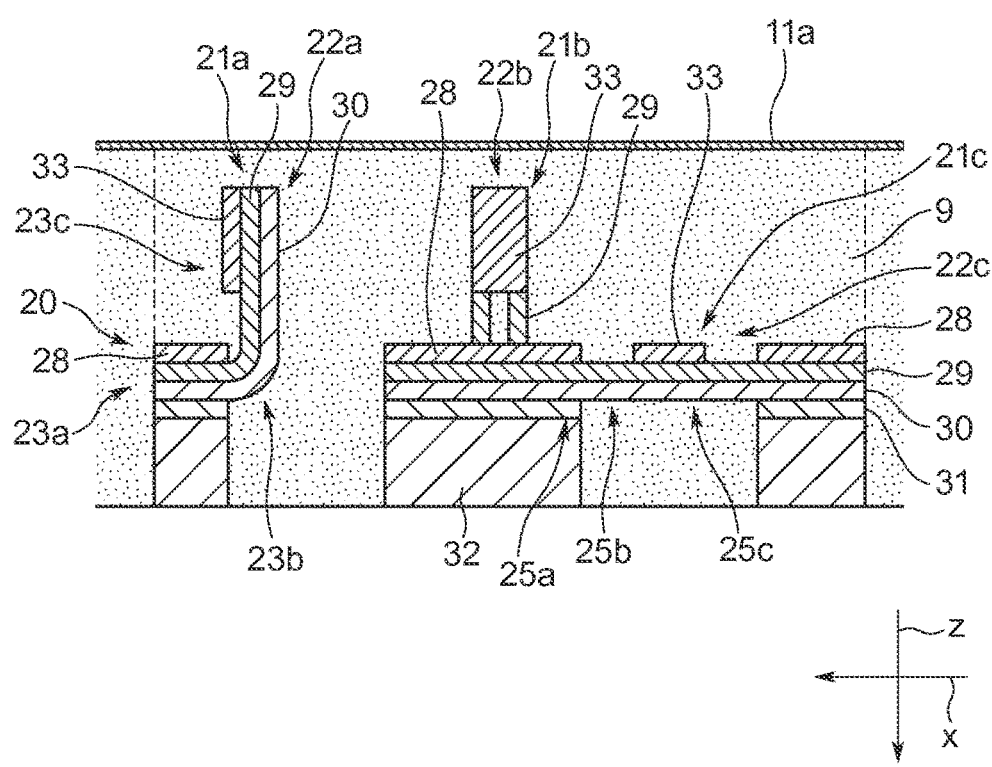
FIG. 12 is a schematic representation showing a detailed configuration of the sensor element when no external force is applied to the sensor element.
Figure 13:
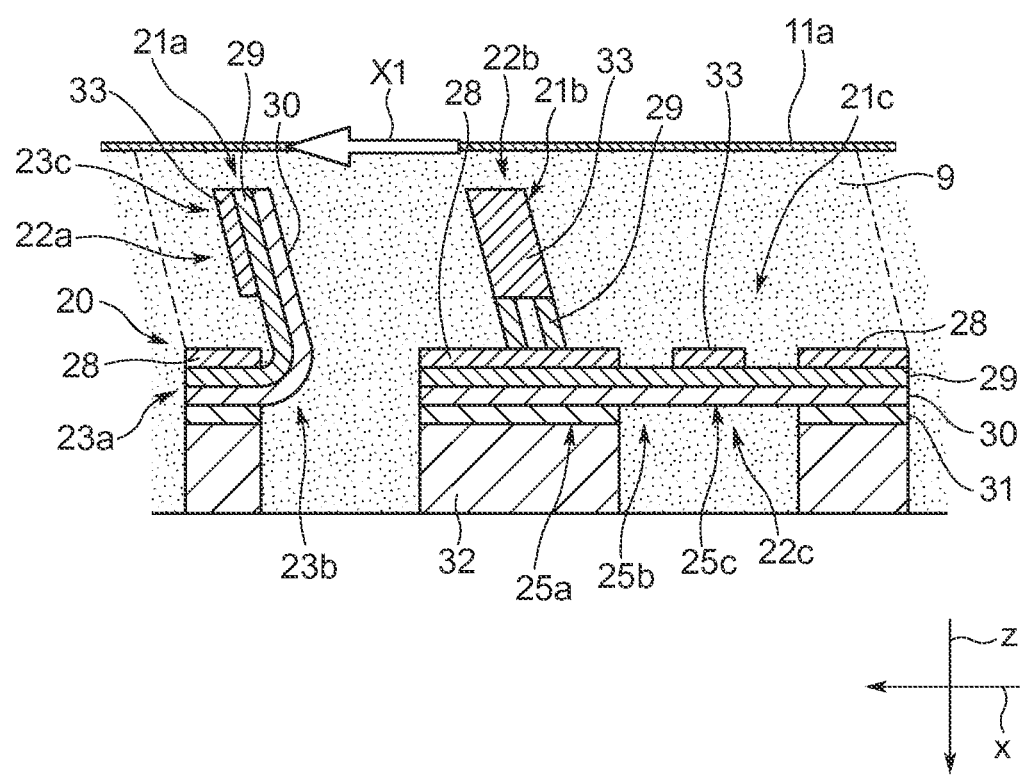
FIG. 13 is a schematic representation showing a state of the sensor element when a front-rear shearing stress is applied in the oral cavity front-rear direction.

Next, as shown in FIG. 13 in which portions corresponding to the portions of FIG. 12 are denoted by the same reference numerals and characters, when a front-rear shearing stress (shown by an arrow X1 in FIG. 13) in the oral cavity front-rear direction x is applied to the coating film 11a of the sensor main body 2 attached to the palate PL, for example, from the tongue TG or food FD, the coating film 11a and the elastic body 9 of the sensor main body 2 can be moved and displaced in the oral cavity front-rear direction x by the front-rear shearing stress received from the oral cavity front-rear direction x. Thereby, in the sensor element 7, the first sensor section 21a, in which the surface portion of the movable section 23c is orthogonal to the oral cavity front-rear direction x, receives, by the movable section 23c, the elastic body 9 moved in the oral cavity front-rear direction x. Thereby, in the sensor element 7, the cantilever section 22a is tilted in the oral cavity front-rear direction x according to the displacement of the elastic body 9, and the resistance value of the piezoresistive layer 29 of the hinge section 23b in the first sensor section 21a can be changed in correspondence with the displacement of the piezoresistive layer 29.

Incidentally, in the sensor element 7, the movable section 23c of the second sensor section 21b is also erected in the elastic body 9, and the cantilever section 22b can also be tilted in the oral cavity front-rear direction x according to the displacement of the elastic body 9 moved in the oral cavity front-rear direction x. However, in the second sensor section 21b, one of the pair of hinge sections 23b can be extended to increase the resistance value, and on the other hand, the other of the pair of hinge sections 23b can be contracted to reduce the resistance value. At this time, in the second sensor section 21b, the increase in the resistance value in the one of the hinge sections 23b is equal to the reduction in the resistance value of the other of the hinge sections 23b. Therefore, when the increase in the resistance value and the reduction in the resistance value are added to each other, the resistance value change as a whole can become zero. In this way, when a front-rear shearing stress is applied to the sensor main body 2 in the oral cavity front-rear direction x from the tongue TG or food FD, the front-rear shearing stress applied in the oral cavity front-rear direction x can be specified on the basis of the resistance value change generated by the first sensor section 21a.

On the other hand, when a left-right shearing stress in the oral cavity left-right direction y is applied to the coating film 11a of the sensor main body 2 attached to the palate PL, for example, from the tongue TG or food FD, the coating film 11a and the elastic body 9 of the sensor main body 2 can be moved and displaced in the oral cavity left-right direction y by the left-right shearing stress received from the oral cavity left-right direction y. Thereby, in the sensor element 7, the second sensor section 21b, in which the surface portion of the movable section 23c is orthogonal to the oral cavity left-right direction y, receives, by the movable section 23c, the elastic body 9 moved in the oral cavity left-right direction y. Thereby, in the sensor element 7, the cantilever section 22b of the second sensor section 21b can be tilted in the oral cavity left-right direction y according to the displacement of the elastic body 9. In this way, in the sensor element 7, the piezoresistive layer 29 of the hinge section 23b in the second sensor section 21b is displaced, so that the left-right shearing stress applied in the oral cavity left-right direction y can be specified on the basis of the resistance value change generated by the displacement of the piezoresistive layer 29.

Incidentally, similarly to the above, at this time, in the first sensor section 21a, one of the pair of hinge sections 23b can be extended to increase the resistance value, and on the other hand, the other of the pair of hinge sections 23b can be contracted to reduce the resistance value. Therefore, when the increase in the resistance value and the reduction in the resistance value are added to each other, the change in the resistance value as a whole can become zero. In this way, when a left-right shearing stress is applied to the sensor main body 2 in the oral cavity left-right direction y from the tongue TG or food FD, the left-right shearing stress applied in the oral cavity left-right direction y can be specified on the basis of the resistance value change generated by the second sensor section 21b.

Figure 14:
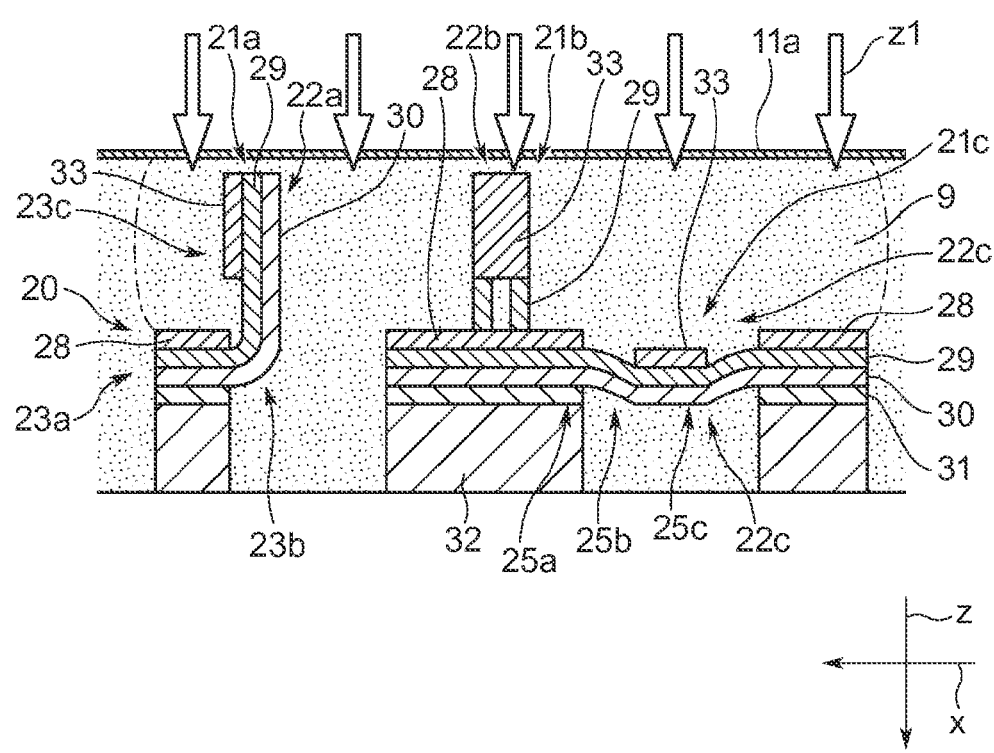
FIG. 14 is a schematic representation showing a state of the sensor element when a vertical pressure is applied in the oral cavity vertical direction.

Further, as shown in FIG. 14 in which portions corresponding to the portions of FIG. 12 are denoted by the same reference numerals and characters, when a vertical pressure (shown by an arrow Z1 in FIG. 14) in the oral cavity vertical direction z is applied to the coating film 11a of the sensor main body 2 attached to the palate PL, for example, from the tongue TG or food FD, the coating film 11a and the elastic body 9 of the sensor main body 2 are recessed in the oral cavity vertical direction z by the vertical pressure received from the oral cavity vertical direction z. Thereby, in the sensor element 7, the third sensor section 21c, in which the surface portion of the movable section 25c is orthogonal to the oral cavity vertical direction z, receives, by the movable section 25c, the elastic body 9 moved in the oral cavity vertical direction z. Thereby, in the sensor element 7, the cantilever section 22c of the third sensor section 21c is recessed according to the displacement of the elastic body 9, and the piezoresistive layer 29 of the hinge section 25b is displaced in correspondence with the amount of recess of the cantilever section 22c. On the basis of the resistance value change generated at this time, the sensor element 7 can specify the vertical pressure applied in the oral cavity vertical direction z.

Incidentally, in the sensor element 7, the surface portion of the movable section 23c of each of the first sensor section 21a and the second sensor section 21b is arranged in parallel with the oral cavity vertical direction z, and hence it is difficult for the surface portion of the movable section 23c to receive the elastic body 9 displaced in the oral cavity vertical direction z. For this reason, in the sensor element 7, when the elastic body 9 is displaced in the oral cavity vertical direction z, mainly the third sensor section 21c can be greatly displaced in association with the elastic body 9. In this way, when a vertical pressure is applied to the sensor main body 2 in the oral cavity vertical direction z from the tongue TG or food FD, the third sensor section 21c can be mainly deformed, so that the vertical pressure applied in the oral cavity vertical direction z can be specified on the basis of a resistance value change generated by the deformation of the third sensor section 21c.

In this way, in the oral cavity sensor, the sensor element 7 is configured to be able to measure a complicated external force applied from the tongue TG or food FD by dividing the external force into external force components in the three axis directions in such a manner that the front-rear shearing stress applied in the oral cavity front-rear direction x can be specified mainly on the basis of a change in the resistance value of first sensor section 21a, that the left-right shearing stress applied in the oral cavity left-right direction y can be specified mainly on the basis of a change in the resistance value of the second sensor section 21b, and that the pressure applied in the oral cavity vertical direction z can be specified mainly on the basis of a change in the resistance value of the third sensor section 21c.

(5) Verification Test

Figure 15A:
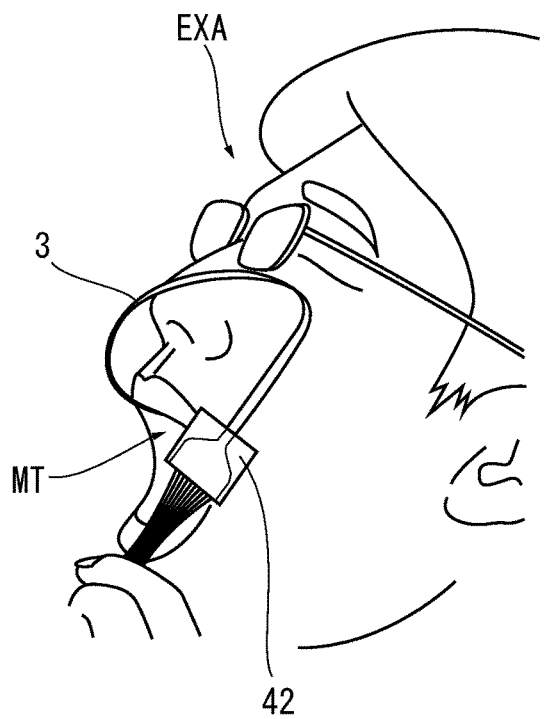
FIG. 15A is a photograph showing an example when the oral cavity sensor is attached to a palate of a subject.
Figure 15B:
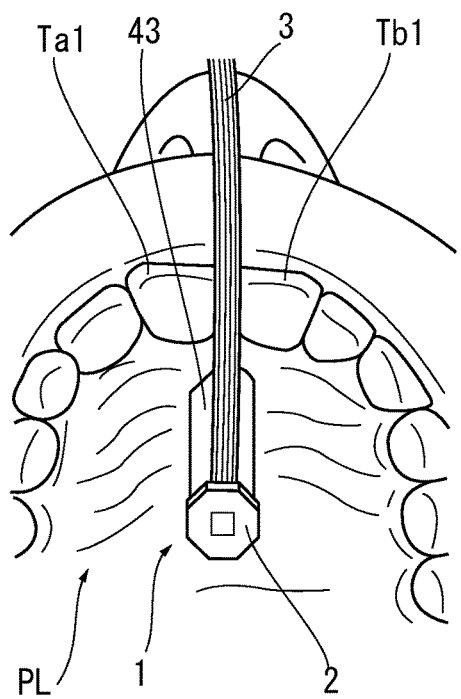
FIG. 15B is a photograph showing an example when the oral cavity sensor is attached to a palate of a subject.

Next, the oral cavity sensor 1 manufactured by the "(3) manufacturing method of sensor element and oral cavity sensor" described above was prepared and attached in the oral cavity MT of the subject EXA as shown in FIG. 15A and FIG. 15B. Then, the subject EXA was made to swallow usual water (hereinafter referred to as indifferent water) having viscosity of 1 [mPa·s], that is, having almost no viscosity, and to swallow water (hereinafter referred to as increased-viscosity water) having predetermined viscosity of 800 [mPa·s] obtained by adding an thickening agent (product name "Toromeiku SP", Meiji Co., Ltd.) into indifferent water. Then, the measurement results obtained by the oral cavity sensor 1 at this time were studied, respectively.

In practice, in this verification test, the sensor main body 2 of the oral cavity sensor 1 was bonded on the raphe palati of the palate PL (hard palate) by a denture stabilizer (product name "Touch Correct II", Shionogi & Co., Ltd.) 43 as shown in FIG. 15B. It should be noted that the wiring body 3 extending from the sensor main body 2 was also bonded from the sensor main body 2 along the raphe palati by the denture stabilizer (product name "Touch Correct II", Shionogi & Co., Ltd.) 43. Further, the wiring body 3 was drawn out, as it was, from the back side of the upper central incisors (upper front teeth) Ta1 and Tb1 to the outside of the oral cavity MT. Incidentally, in this verification test, the wiring body 3 was stably held, as shown in FIG. 15A, in such a manner that the end portion of the wiring body 3 was connected to a wiring body holding substrate 42, and that the wiring body 3 drawn out from the oral cavity MT was folded back on the nose of the subject EXA, and further the wiring body holding substrate 42 was bonded around the mouth.

Next, in this state, plain water having different amounts of 5 [ml], 10 [ml], 15 [ml], and 20 [ml] were prepared, and the subject EXA was made to swallow the plain water at room temperature having different amounts. The measurement results obtained from the oral cavity sensor 1 at this time were investigated, and the results shown in (a), (b) and (c) of FIG. 16 were obtained.

Figure 16:
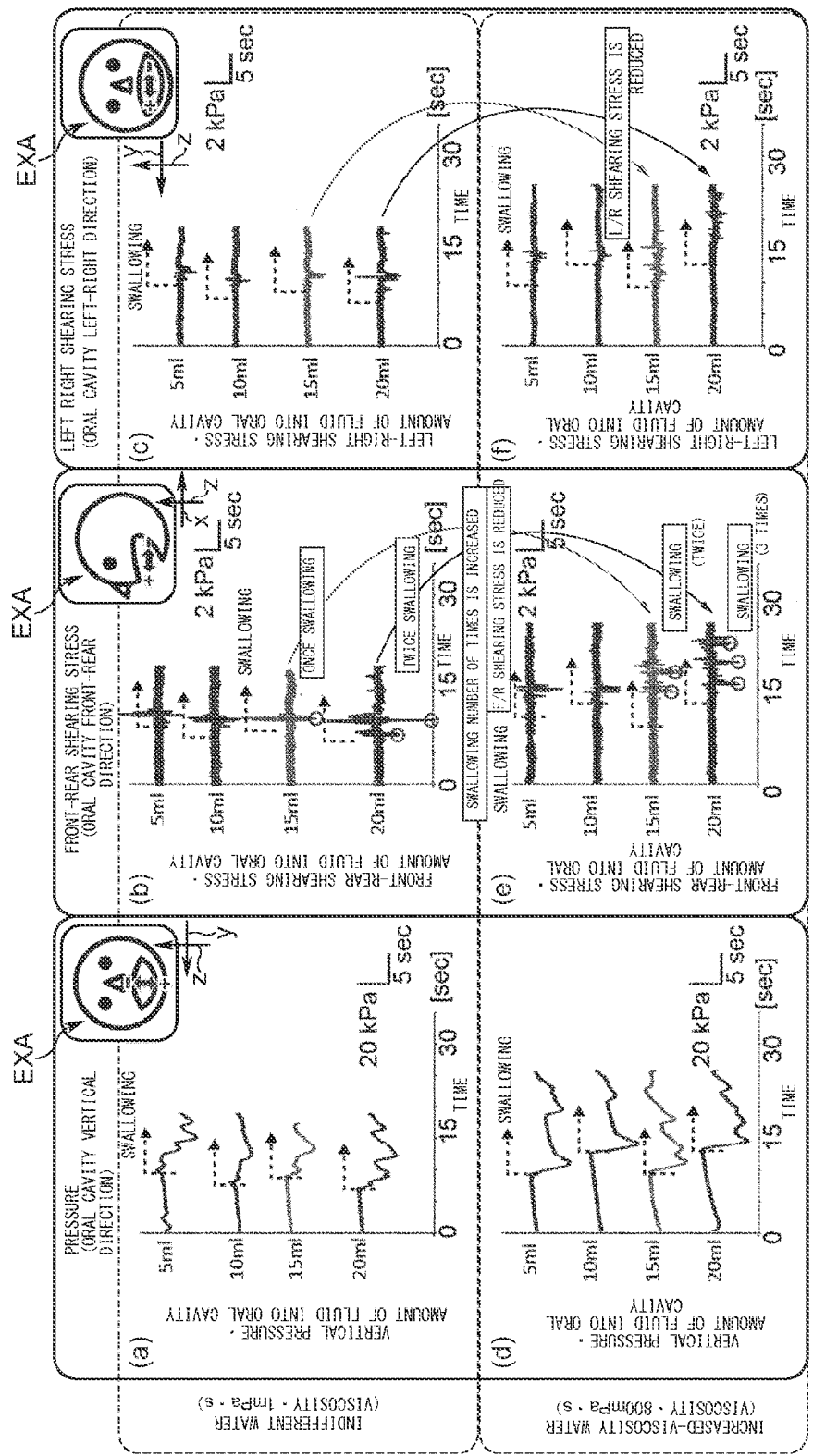
FIG. 16 shows graphs respectively showing front-rear shearing stress, left-right shearing stress, and vertical pressure when indifferent water and increased-viscosity water are swallowed.

Here, FIG. 16(a) shows measurement results obtained by the third sensor section 21c and showing the vertical pressure applied in the oral cavity vertical direction z. Further, FIG. 16(b) shows measurement results obtained by the first sensor section 21a and showing the front-rear shearing stress applied in the oral cavity front-rear direction x. Further, FIG. 16(c) shows measurement results obtained by the second sensor section 21b and showing the left-right shearing stress applied in the oral cavity left-right direction y. Further, each of the dotted lines shown in (a), (b) and (c) of FIG. 16 shows a timing when the subject EXA swallowed the indifferent water.

Further, apart from this, increased-viscosity water having different amounts of 5 [ml], 10 [ml], 15 [ml], and 20 [ml] were prepared, and the subject EXA was made to swallow the increased-viscosity water at room temperature having different amounts. The measurement results obtained from the oral cavity sensor 1 at this time were investigated, and the results shown in (d), (e) and (f) of FIG. 16 were obtained.

Here, FIG. 16(d) shows measurement results obtained by the third sensor section 21c and showing the vertical pressure applied in the oral cavity vertical direction z. Further, FIG. 16(e) shows measurement results obtained by the first sensor section 21a and showing the front-rear shearing stress applied in the oral cavity front-rear direction x. Further, FIG. 16(f) shows measurement results obtained by the second sensor section 21b and showing the left-right shearing stress applied in the oral cavity left-right direction y. Further, each of the dotted lines shown in (d), (e) and (f) of FIG. 16 shows a timing when the subject EXA swallowed the increased-viscosity water.

From (a) and (d) of FIG. 16, it was confirmed that, when the viscosity of fluid is increased, the vertical pressure, which is applied to the palate PL in the oral cavity vertical direction z at the time when the subject EXA swallows the fluid, is increased. However, from (b) and (e) of FIG. 16, it was confirmed that, when the viscosity of the fluid is increased, the front-rear shearing stress applied to the palate PL in the oral cavity front-rear direction x is reduced.

Here, as shown in FIG. 16(b), for example, when 15 [ml] of indifferent water in the oral cavity MT was swallowed, it was confirmed that a large peak appears at one place in the waveform representing the front-rear shearing stress applied in the oral cavity front-rear direction x, and hence that the subject EXA performed swallowing once. On the other hand, as shown in FIG. 16(e), when the same amount of increased-viscosity water of 15 [ml] was swallowed, it was confirmed that a large peak appear at two places in the waveform representing the front-rear shearing stress applied in the oral cavity front-rear direction x, and hence that the subject EXA performed swallowing twice.

Further, as shown in FIG. 16(b), for example, when 20 [ml] of indifferent water in the oral cavity MT was swallowed, it was confirmed that a large peak appear at two places in the waveform representing the front-rear shearing stress applied in the oral cavity front-rear direction x, and hence that the subject EXA performed swallowing twice. On the other hand, as shown in FIG. 16(e), when the same amount of increased-viscosity water of 20 [ml] was swallowed, it was confirmed that a large peak appear at three places in the waveform representing the front-rear shearing stress applied in the oral cavity front-rear direction x, and hence that the subject EXA performed swallowing three times.

From this, it was confirmed that, when the viscosity of the fluid is increased, the number of times of swallowing is increased, but the front-rear shearing stress generated in the oral cavity front-rear direction x is reduced. In this way, it was confirmed that, with the oral cavity sensor 1 which can measure the front-rear shearing stress in the oral cavity front-rear direction x in addition to the vertical pressure in the oral cavity vertical direction z, it is possible to analyze detailed tongue movements which could not be sufficiently analyzed only by the vertical pressure in the oral cavity vertical direction z.

Further, from FIG. 16(c) and (f), it was confirmed that, when the viscosity of the fluid is increased, the left-right shearing stress applied to the palate PL in the oral cavity left-right direction y is reduced. In this way, it was confirmed that, from the movements of the tongue which moves in a complicated manner at the time of swallowing, the front-rear shearing stress, the left-right shearing stress, and the vertical pressure, which respectively act in the three axis directions of the oral cavity front-rear direction x, the oral cavity left-right direction y, and the oral cavity vertical direction z, can be individually measured by the oral cavity sensor 1.

Further, from the measurement results in the three axis directions as shown in FIG. 16, it could be inferred that, for example, at the time of swallowing indifferent water, the indifferent water is made to flow into the throat by gravity in a state where the tongue TG is brought into close contact with the palate toward the oral cavity vertical direction z to prevent the indifferent water from leaking from the tip of the tongue to the outside of the oral cavity MT. Further, on the other hand, it was possible to infer a principle of tongue movements in the oral cavity MT at the time of swallowing, such as, for example, a principle that, when the fluid with increased viscosity is swallowed, the fluid is sent into the throat by the tongue movements in a state where the tongue is brought into closer contact with the palate also in the oral cavity front-rear direction x and the oral cavity left-right direction y. The above-described inference of tongue movements at the time of swallowing assists the development of food which can be easily swallowed by elderly people, and the like, having swallowing difficulty, and provides analysis results important for future development of food.

(6) Operation and Effect

In the above-described configuration, the oral cavity sensor 1 is configured such that the sensor element 7, which can measure each of the external force components in the three axis directions, that is, each of the front-rear shearing stress in the oral cavity front-rear direction x, the left-right shearing stress in the oral cavity left-right direction y, and the vertical pressure in the oral cavity vertical direction z, is embedded in the elastically deformable elastic body 9, and such that the elastic body 9 is further covered with the coating film 11a made of parylene.

Thereby, in the oral cavity sensor 1 which is even provided with the sensor element 7 having a mechanical configuration capable of measuring each of the external force components in the three axis directions, the sensor element 7 can be protected by the elastic body 9. Further, the elastic body 9 as a whole is covered with the coating film 11a made of a biocompatible material, and hence the sensor element 7 and the elastic body 9 can be safely attached in the oral cavity MT of the subject EXA, so as to measure each of the external force components in the three axis directions. Thereby, on the basis of each of the external force components in the three axis directions, complicated tongue movements at the time of mastication or swallowing in the oral cavity MT can be analyzed in more detail than before.

Further, in the oral cavity sensor 1, the elastic body 9 as a whole is covered with the coating film 11a, and thereby even a certain mechanical strength can also be given to the elastic body 9. Also, the coating film 11a prevents that the tongue TG which moves in a complicated manner in the oral cavity MT, and food FD are brought into direct contact with the elastic body 9. Thereby, the elastic body 9 can be prevented from being damaged at the time of mastication or swallowing. As a result, the subject EXA does not have to worry about damage to the sensor main body 2, and can perform natural mastication or swallowing.

In practice, in the oral cavity sensor 1, when the tongue TG or food FD comes into contact with the sensor main body 2 at the time of mastication or swallowing, the elastic body 9 is thereby elastically deformed. In association with the state of displacement of the elastic body 9, it is possible to obtain, from the sensor element 7, measurement results of the front-rear shearing stress in the oral cavity front-rear direction x, the left-right shearing stress in the oral cavity left-right direction y, and the vertical pressure in the oral cavity vertical direction z.

Further, in the oral cavity sensor 1, the back surface of the main-body-side flexible substrate 6 is also covered with the elastic body 9 so that the sensor element 7 is attached in the oral cavity MT of the subject EXA via the elastic body 9. Thereby, in the oral cavity sensor 1, when the sensor main body 2 is bonded to the palate PL, the elastic body 9 in the sensor main body 2 is flexibly deformed in correspondence with the uneven shape of the palate PL, and hence the sensor main body 2 can be surely brought into close contact with and attached to the uneven palate PL.

Further, in the oral cavity sensor 1, similarly to the sensor main body 2, the wiring body 3 drawn out from the sensor main body 2 is also covered with the coating film 11b made of parylene which is a biocompatible material. Thereby, in the oral cavity sensor 1, similarly to the sensor main body 2, the wiring body 3 can also be safely attached in the oral cavity MT, so that, in a state where the sensor main body 2 is bonded at an optimal position of the palate PL, measurement results from the sensor main body 2 can be sent out to an external measurement apparatus by the wiring body 3. Also, in the oral cavity sensor 1, the mechanical strength of the wiring body 3 can be improved by the coating film 11b, so that, when the wiring body 3 is drawn out from the upper central incisors Ta1 and Tb1 as shown in FIG. 1, and even when the wiring body 3 is accidentally masticated by the subject EXA at the time of mastication, the wiring 14 can be prevented from being damaged.

Further, in the oral cavity sensor 1, the first sensor section 21a, the second sensor section 21b, and the third sensor section 21c are formed so as to be adjacent to each other on the base section 20 and to satisfy a positional relationship between three vertexes of a triangle. The three sections of the first sensor sections 21a, the second sensor sections 21b, and the third sensor sections 21c are efficiently arranged on the base section 20 and formed so as to be collected in the oral cavity without being away from each other. Thereby, in the sensor main body 2, the size of the sensor element 7 can be reduced, and the bonding area of the palate PL can be made relatively small. Thereby, in the oral cavity sensor 1, even when the sensor main body 2 is bonded to the palate PL, the sensor main body 2 does not become an obstacle at the time of mastication or swallowing, so as to enable the subject EXA to naturally perform mastication or swallowing.

Incidentally, in the oral cavity sensor 1, it is only necessary that resistance value changes obtained from three places of the first sensor section 21a, the second sensor section 21b, and the third sensor section 21c can be measured. Thereby, the number of the wirings provided in the wiring body 3 can be reduced, so that the width of the wiring body 3 can be reduced as much as possible, and also the thickness of the wiring body 3 can be reduced. In this way, in the oral cavity sensor 1, the width and thickness of the wiring body 3 are reduced, so that, when the wiring body 3 is bonded in the oral cavity MT, the sense of discomfort of the subject EXA can be reduced. Further, in the oral cavity sensor 1, the width and thickness of the wiring body 3 can be reduced, so that, in the case where the subject EXA has the gap G1 between the upper central incisor Ta1 and the lower central incisor Ta10, the wiring body 3 does not have to be routed in the oral cavity MT in a complicated manner, and the wiring body 3 can be simply drawn out, as it is, from the gap G1 to the outside of the oral cavity MT by being linearly extended along the raphe palati C1 from the palate PL to which the sensor main body 2 is bonded.

(7) Another Embodiment (7-1) Sensor Element Provided with Temperature Sensor Section It should be noted that the present invention is not limited to the above described embodiment, and various modifications are possible within the scope and spirit of the present invention. For example, in the above-described embodiment, a case is described, in which the sensor element 7 is applied, the sensor element 7 being provided with the first sensor section 21a configured to measure the front-rear shearing stress, the second sensor section 21b configured to measure the left-right shearing stress, and the third sensor section 21c configured to measure the vertical pressure. However, the present invention is not limited to this, and a sensor element may also be applied to the present invention, which sensor element is provided with the first sensor section 21a configured to measure the front-rear shearing stress, the second sensor section 21b configured to measure the left-right shearing stress, and the third sensor section 21c configured to measure the vertical pressure, and in addition is provided with a temperature sensor section configured to measure a resistance value change generated by the displacement of a piezoresistive layer caused by a temperature change.

Figure 17:
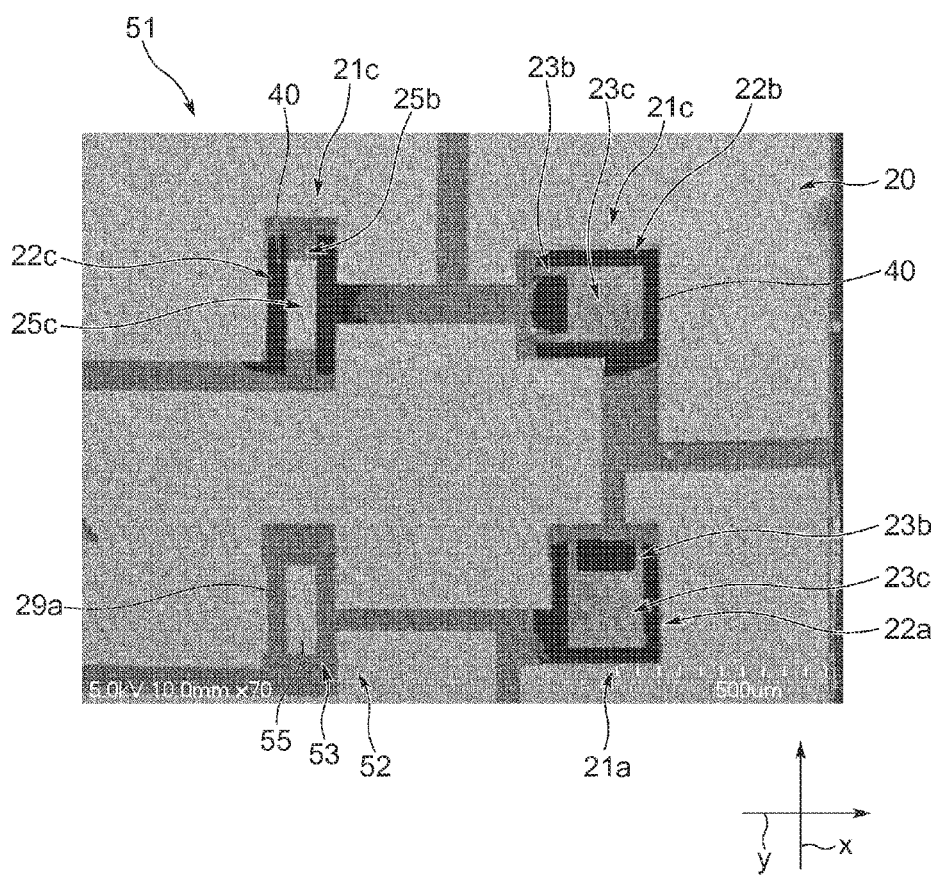
FIG. 17 is an SEM image showing a sensor element according to a second embodiment.
Figure 18:
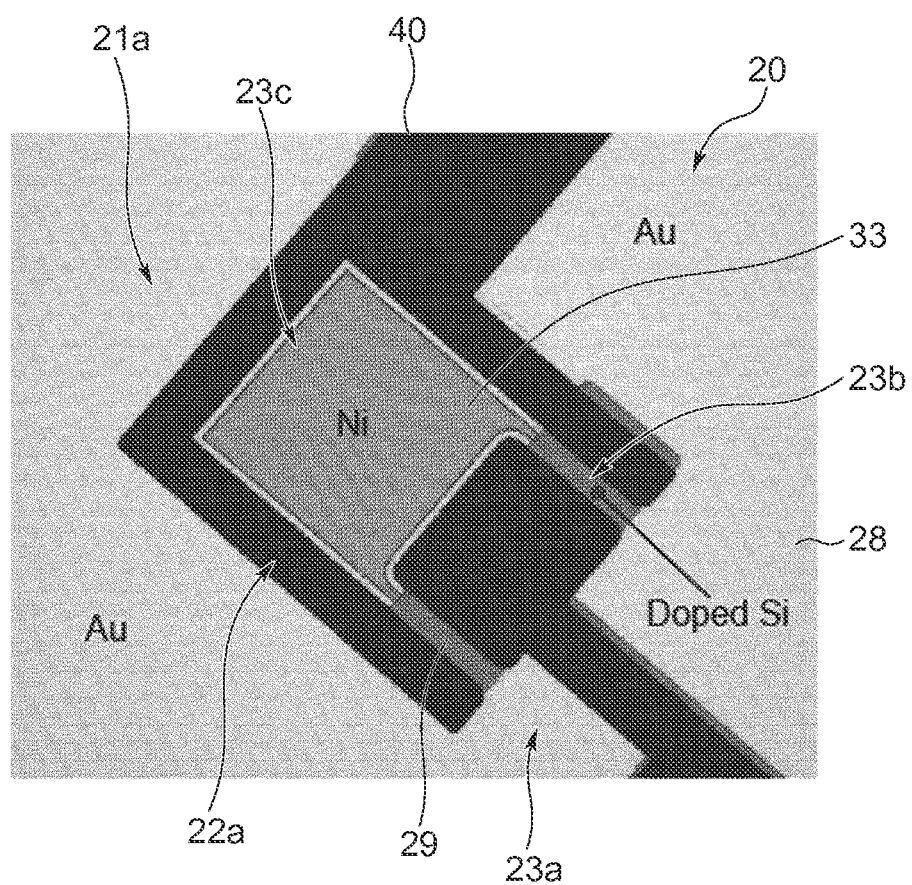
FIG. 18 is an SEM image showing a configuration of a first sensor section.

In this case, as shown in FIG. 17 in which components corresponding to the components shown in FIG. 4 are denoted by the same reference numerals and characters, in a sensor element 51, the first sensor section 21a, the second sensor section 21b, and the third sensor section 21c are formed on the base section 20, and also a temperature sensor section 52 is formed on the base section 20. It should be noted that, in the case of the present embodiment, the sensor element 51 is configured such that the first sensor section 21a, the second sensor section 21b, the third sensor section 21c, and the temperature sensor section 52 are formed to satisfy a positional relationship between four vertexes of a quadrilateral, and thereby the four sections of the first sensor section 21a, the second sensor section 21b, the third sensor section 21c, and the temperature sensor section 52 are efficiently arranged in the limited area of the sensor element 51. It should be noted that, in FIG. 17 and FIG. 18 described below, the movable section 23c of each of the first sensor section 21a and the second sensor section 21b apparently seems to be formed to be flush with the base section 20, but in practice, the movable section 23c of each of the first sensor section 21a and the second sensor section 21b is erected with respect to the base section 20.

Actually, in the sensor element 51, as described above, each of the movable sections 23c and 25c of the first sensor section 21a, the second sensor section 21b, and the third sensor section 21c is formed as a free end in the opening region 40 of the base section 20 so as to be able to be displaced according to an external force from a predetermined direction. Here, FIG. 18, in which components corresponding to the components shown in FIG. 12 are denoted by the same reference numerals and characters, shows an SEM image of the first sensor section 21a in which the cantilever section 22a is arranged in the opening region 40, and in which, in the cantilever section 22a, the Au/Ni thin film 33 is formed in the movable section 23c, and the piezoresistive layer (Doped Si) 29 is provided in each of the pair of hinge sections 23b.

Figure 19:
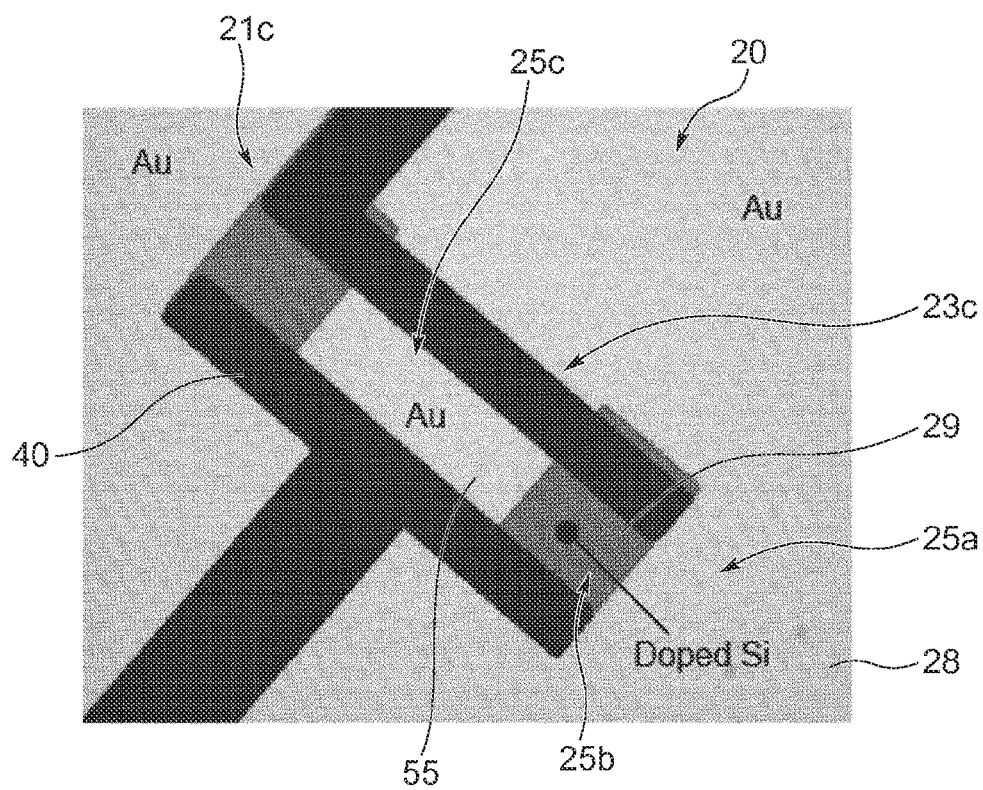
FIG. 19 is an SEM image showing a configuration of a third sensor section.

On the other hand, FIG. 19 shows an SEM image of the third sensor section 21c in which the both-end supported beam-shaped cantilever section 22c is arranged in the opening region 40, in which, in the cantilever section 22c, an Au thin film 55 is formed in the movable section 25c, and in which the piezoresistive layer (Doped Si) 29 is formed in each of the pair of hinge sections 25b. On the other hand, in the temperature sensor section 52, as shown in FIG. 17, a quadrilateral-shaped movable section 53 is formed to be flush with the base section 20. A piezoresistive layer 29a is formed in the whole peripheral region of the movable section 53 so as to surround the movable section 53, and no opening region is formed. Thereby, in the temperature sensor section 52, unlike the third sensor section 21c, even when a pressure is applied in the oral cavity vertical direction z, the piezoresistive layer 29a is not deformed, and hence the movable section 53 is not recessed, so that the surface portion of the movable section 53 can be maintained to be flush with the base section 20.

In this way, in the temperature sensor section 52, the movable section 53 is not moved even when an external force is applied. However, when the temperature surrounding the temperature sensor section 52 is changed, the piezoresistive layer 29a around the movable section 53 is displaced according to the temperature change. Thereby, in the temperature sensor section 52, the resistance value can be changed in correspondence with the displacement of the piezoresistive layer 29a. Here, the resistance value change according to the temperature change is also caused in the piezoresistive layer 29 of each of the hinge sections 23b and 25b of the first sensor section 21a, the second sensor section 21b, and the third sensor section 21c. That is, each of the first sensor section 21a, the second sensor section 21b, and the third sensor section 21c measures the resistance value change in the piezoresistive layer 29, the resistance value change being caused by application of an external force, and also measures the resistance value change corresponding to the displacement of the piezoresistive layer 29, the displacement being caused according to the temperature of swallowed food.

To cope with this, in the sensor element 51, the temperature dependent portion of the resistance value change in the piezoresistive layer 29a, the portion being measured by the temperature sensor section 52, is removed from the resistance value change measured from each of the first sensor section 21a, the second sensor section 21b, and the third sensor section 21c. Thereby, in the sensor element 51, the temperature dependent portion of the resistance value change can be eliminated from the measurement result of each of the first sensor section 21a, the second sensor section 21b, and the third sensor section 21c, so that only the resistance value change generated by the external force applied from the tongue TG or food FD at the time of mastication or swallowing can be measured.

In the above-described configuration, the sensor element 51 is provided with the temperature sensor section 52 capable of measuring only a resistance value change in the piezoresistive layer 29a according to a temperature change, and is configured such that the resistance value change measured by the temperature sensor section 52 is eliminated (subtracted) from the resistance value change measured from each of the first sensor section 21a, the second sensor section 21b, and the third sensor section 21c. Thereby, in the sensor element 51, only the resistance value change generated by the external force applied from the tongue TG or food FD at the time of mastication or swallowing can be measured in the state in which the temperature dependent portion of the resistance value change is eliminated. Thereby, on the basis of each of external force components in the three axis directions, complicated tongue movements in the oral cavity MT at the time of mastication or swallowing can be analyzed in more detail than before.

(7-2) Other Modifications

Figure 20:
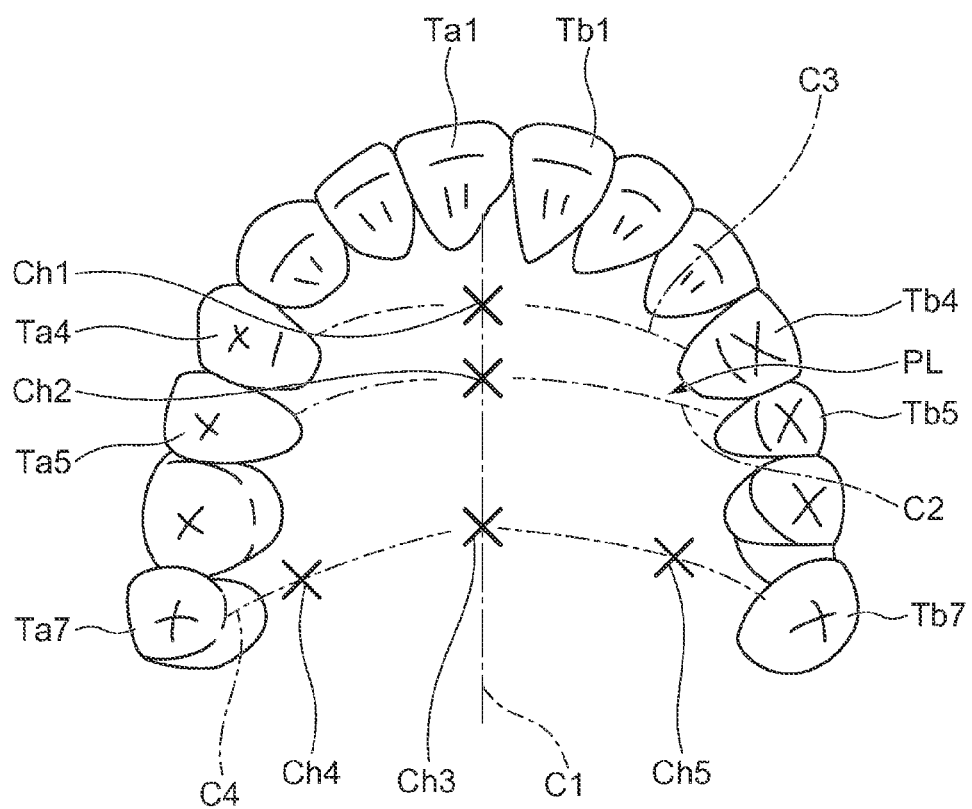
FIG. 20 is a schematic representation showing various positions at which the oral cavity sensor is bonded to the palate.

Further, in the above-described embodiment, as shown in FIG. 20, a case is described, where the sensor main body 2 is bonded at a position Ch2 at which the raphe palati C1 passing through the median line of the palate (hard palate) PL crosses the virtual line C2 connecting between the second premolars Ta5 and Tb5 and extending in the oral cavity left-right direction y. However, the present invention is not limited to this, and the sensor main body 2 may be bonded at other various predetermined positions on the raphe palati C1, such as, for example, a position Ch1 at which the raphe palati C1 crosses a virtual line C3 connecting between first premolars Ta4 and Tb4 and extending in the oral cavity left-right direction y, and a position Ch3 at which the raphe palati C1 crosses a virtual line C4 connecting between second molars Ta1 and Tb7 and extending in the oral cavity left-right direction y. Further, the sensor main body 2 may be provided not only on the raphe palati C1 but also at various positions located on the virtual line C4 and deviated from the raphe palati C1, for example, positions Ch4 and Ch5 close to the second molars Ta1 and Tb7, and at various positions on the virtual lines C2 and C3. Alternatively, the sensor main body 2 may be bonded at various positions, such as the upper central incisors Ta1 and Tb1, or the second premolars Ta5 and Tb5, other than positions of the mucous membrane in the oral cavity MT, as long as the positions can come into contact with the tongue TG in the oral cavity MT.

Figure 21A:
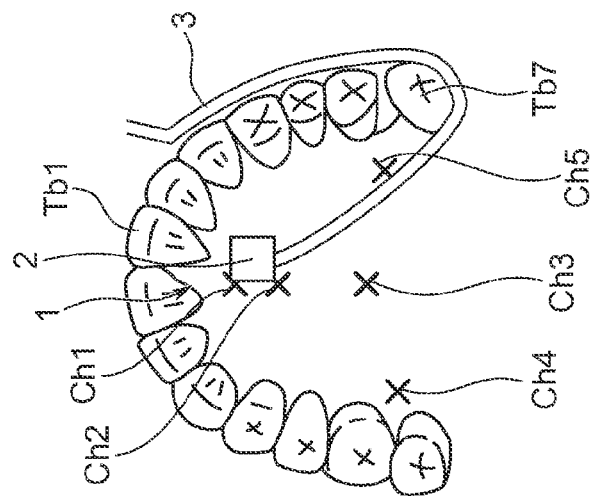
FIG. 21A is a schematic representation showing a modification at the time when a wiring of the oral cavity sensor is routed in the oral cavity.

Further, in the above-described embodiment, a case is described, in which the wiring body 3 of the oral cavity sensor 1 is linearly drawn out from the sensor main body 2 to the outside of the oral cavity MT along the raphe palati C1 through the back side of the upper central incisors Ta1 and Tb1. However, the present invention is not limited to this, and for example, as shown in FIG. 21A, the wiring body 3 extending from the sensor main body 2 bonded at a fixing position Ch1 or Ch2 may be arranged such that the wiring body 3 is extended along the raphe palati C1 to the fixing position Ch3 of the palate PL and then extended to the side of the second molar Tb7 through the position Ch5, and such that the wiring body 3 is routed around the gum behind the second molar Tb7 and folded toward the side of the upper central incisor Tb1, so as to be drawn out to the outside of the oral cavity MT along the outside of the upper teeth (the second molar, the first molar, the second premolar, and the first premolar).

Figure 21B:
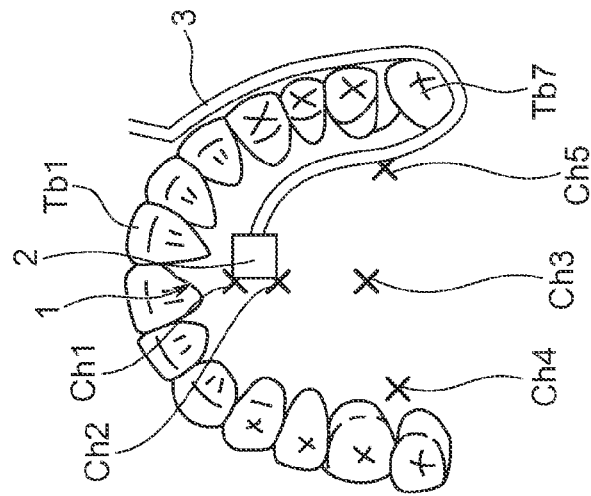
FIG. 21B is a schematic representation showing a modification at the time when a wiring of the oral cavity sensor is routed in the oral cavity.

Further, as another example of routing the wiring body 3, as shown in FIG. 21B, the wiring body 3 extending from the sensor main body 2 bonded at a fixing position Ch1 or Ch2 may be arranged such that the wiring body 3 is routed along the back side of upper teeth (the first premolar, the second premolar, the first molar, and the second molar) to the second molar Tb7 located on the deepest side, and is folded around the gum behind the second molar Tb7 toward the side of the upper central incisor Tb1, so as to be drawn out, as it is, to the outside of the oral cavity MT along the outer side of upper teeth (the second molar, the first molar, the second premolar, and the first premolar).

Figure 21C:
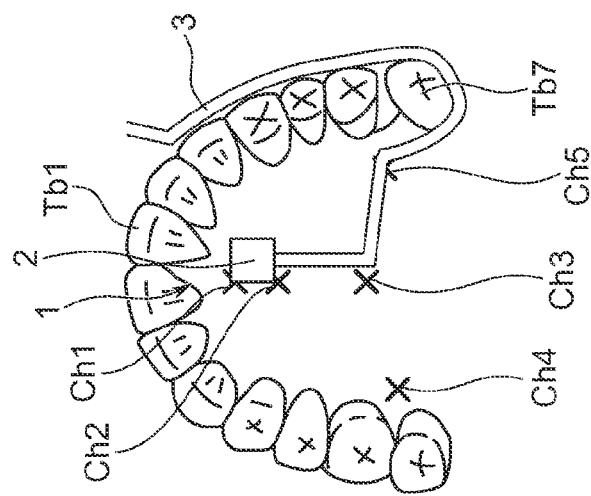
FIG. 21C is a schematic representation showing a modification at the time when a wiring of the oral cavity sensor is routed in the oral cavity.

Further, as another example of routing the wiring body 3, as shown in FIG. 21C, the wiring body 3 extending from the sensor main body 2 bonded at a fixing position Ch1 or Ch2 may be arranged such that the wiring body 3 is linearly extended from the fixing position Ch1 or Ch2 to the second molar Tb7, and is then folded around the behind of the second molar Tb7 toward the side of the upper central incisor Tb1, so as to be drawn out, as it is, to the outside of the oral cavity MT along the outer side of upper teeth (the second molar, the first molar, the second premolar, and the first premolar).

In this way, in the oral cavity sensor 1 according to the present invention, the wiring body 3 can be formed to have a small width and thickness, and hence can be freely routed in a narrow space in the oral cavity MT. Thereby, as described with reference to FIG. 21A to FIG. 21C, the wiring body 3 can be freely routed in correspondence with the shape of the palate and the denture mold of the subject EXA. Further, in the wiring body 3, all of the wiring-side flexible substrate 13 and the wiring 14 are covered with the coating film 11b, and hence the mechanical strength can be improved by the coating film 11b. Therefore, even when the wiring body 3 is freely bent according to the shape of the palate and the denture mold of the subject EXA, the wiring body 3 is hardly damaged, and also the wiring-side flexible substrate 13 and the wiring 14 can be prevented from being damaged.

Further, in the above-described embodiment, a case is described, in which the cantilever-shaped first and second sensor sections 21a and 21b, and the both-end supported beam-shaped third sensor section 21c are provided, so as to measure each of the external force components in the three axis directions at the time when the first sensor section 21a, the second sensor section 21b, and the third sensor section 21c are displaced in association with the displacement of the elastic body 9. However, the present invention is not limited to this, and the first sensor section, the second sensor section, and the third sensor section, which are formed in various shapes, such as, for example, the third sensor section formed into a cantilever shape, may be applied as long as each of the sensor sections has a configuration capable of being deformed according to the displacement of the elastic body 9 and capable of measuring an external force component in each of the three axis directions.

(8) Oral Cavity Sensor Provided with First Sensor Main Body and Second Sensor Main Body In the above-described embodiment, the oral cavity sensor 1 provided with only one sensor main body 2 is described. However, the present invention is not limited to this, and the oral cavity sensor may also be configured to be provided with a plurality of sensor main bodies, such as two or three sensor main bodies. For example, FIG. 22, in which components corresponding to the components shown in FIG. 1 are denoted by the same reference numerals and characters, shows an oral cavity sensor 61 provided with two sensor main bodies, and having a configuration in which a first sensor main body 62a and a second sensor main body 62b are arranged in a row in the oral cavity front-rear direction x.

In practice, in the oral cavity sensor 61, the first sensor main body 62a and the second sensor main body 62b, which are provided at the wiring body 3 so as to be arranged in a row, are bonded to the palate in the oral cavity, so as to be able to come into contact with the tongue, and so as to enable the wiring body 3 to be drawn out to the outside of the oral cavity from the inside of the oral cavity. In the oral cavity sensor 61, the wiring body 3 is connected to a measurement apparatus (not shown) provided outside the oral cavity, so that each of measurement results obtained from the first sensor main body 62a and the second sensor main body 62b can be sent out to the measurement apparatus via the wiring body 3. Thereby, in the measurement apparatus, each of the measurement results obtained from the first sensor main body 62a and the second sensor main body 62b respectively provided in the oral cavity sensor 61 is displayed on a display, and on the basis of the displayed measurement results, movements of the tongue of the subject can be analyzed by being divided into front-rear, left-right, and up-down motions at a front side of the tongue, and into front-rear, left-right, and up-down motions at a rear side of the tongue.

Specifically, in the case of the present embodiment, for example, the first sensor main body 62a is bonded at a position at which the raphe palati C1 of the hard palate occupying two-thirds of the front portion of the palate PL crosses the virtual line C3 connecting between the first premolars Ta4 and Tb4 and extending in the oral cavity left-right direction y. The first sensor main body 62a is also arranged so that the whole surface thereof is easily brought into contact with the front side of the tongue (the distal end side of the tongue). On the other hand, for example, the second sensor main body 62*b* is bonded at a position at which the raphe palati C1 crosses a virtual line C6 connecting between molars Ta6 and Tb6 and extending in the oral cavity left-right direction y. The second sensor main body 62*b* is arranged to measure how the tongue is in contact with the palate.

Figure 23:
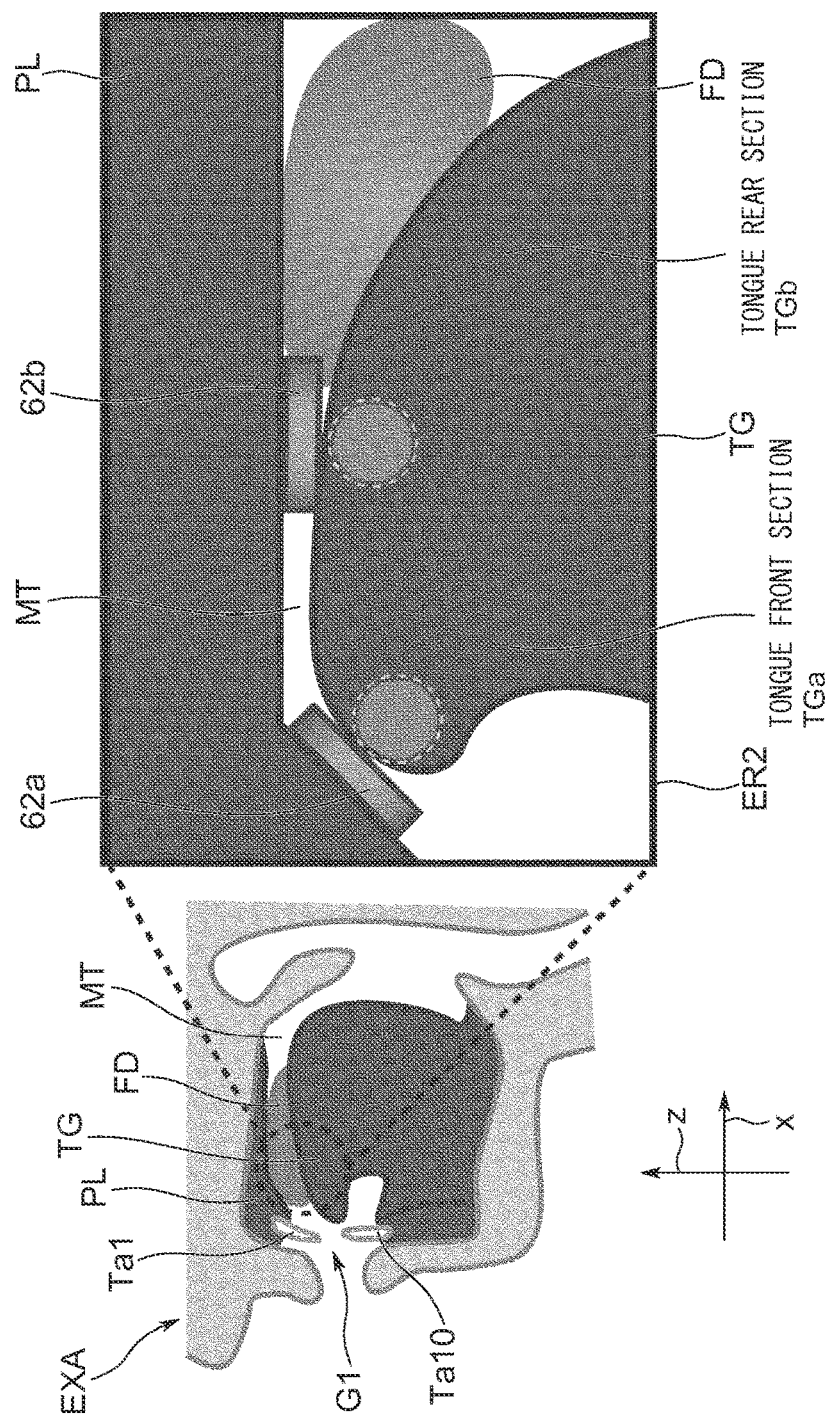
FIG. 23 is a schematic representation showing a state when a subject, to which the oral cavity sensor according to another embodiment is attached, swallows food.

In this way, as shown in FIG. 23, in which components corresponding to the components shown in FIG. 2 are denoted by the same reference numerals and characters, in the oral cavity sensor 61, each of external force components in the three axis directions applied to the palate PL by a tongue front section TGa is measured by the first sensor main body 62*a*, and each of external force components in the three axis directions applied to the palate PL by a tongue rear section TGb is measured by the second sensor main body 62*b*. Thereby, it is possible to analyze what kinds of movements are performed in each of the tongue front section TGa and the tongue rear section TGb at the time of masticating or swallowing.

Figure 24:
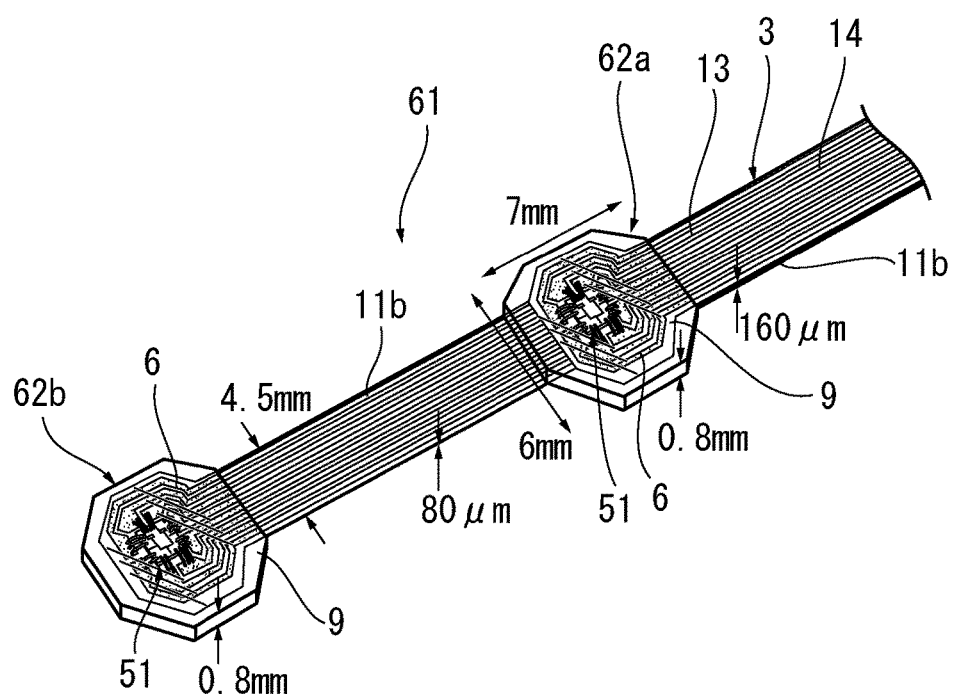
FIG. 24 is a schematic representation showing an entire configuration of an oral cavity sensor according to another embodiment.
Figure 24:
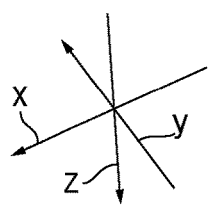

In practice, as shown in FIG. 24, in which components corresponding to the components shown in FIG. 3 are denoted by the same reference numerals and characters, the oral cavity sensor 61 is configured such that the first sensor main body 62*a* and the second sensor main body 62*b* are formed to have the same shape and the same size, such that the first sensor main body 62*a* is arranged at the distal end of the wiring body 3, and such that the second sensor main body 62*b* is arranged on the wiring body 3 so as to be separated from the first sensor main body 62*a* at a predetermined distance. It should be noted that the first sensor main body 62*a* and the second sensor main body 62*b* have the same configuration, and hence the following description will be made focusing on the first sensor main body 62*a*.

The first sensor main body 62*a* is formed to have a flat shape of a width of 6 [mm], a depth of 7 [mm], and a thickness of 0.8 [mm], and to have an octagonal outline shape with rounded corner portions. The first sensor main body 62*a* is configured such that the sensor element (FIG. 17) is installed in the sensor installation surface of the main-body-side flexible substrate 6, and the whole of the main-body-side flexible substrates 6 and the sensor element 51 are covered with the elastic body 9 made of silicone rubber.

It should be noted that, in the case of the present embodiment, a case is described, in which the sensor element 51 also provided with the temperature sensor section 52 (FIG. 17) is applied as the sensor element. However, the present invention is not limited to this, and the sensor element 7 (FIG. 4) may not be provided with the temperature sensor section 52, and may be configured such that the first sensor main body 62*a* and the second sensor main body 62*b* are configured to be different from each other. For example, the sensor element 51 provided with the temperature sensor section 52 may be applied to only one of the first sensor main body 62*a* and the second sensor main body 62*b*.

Figure 22:
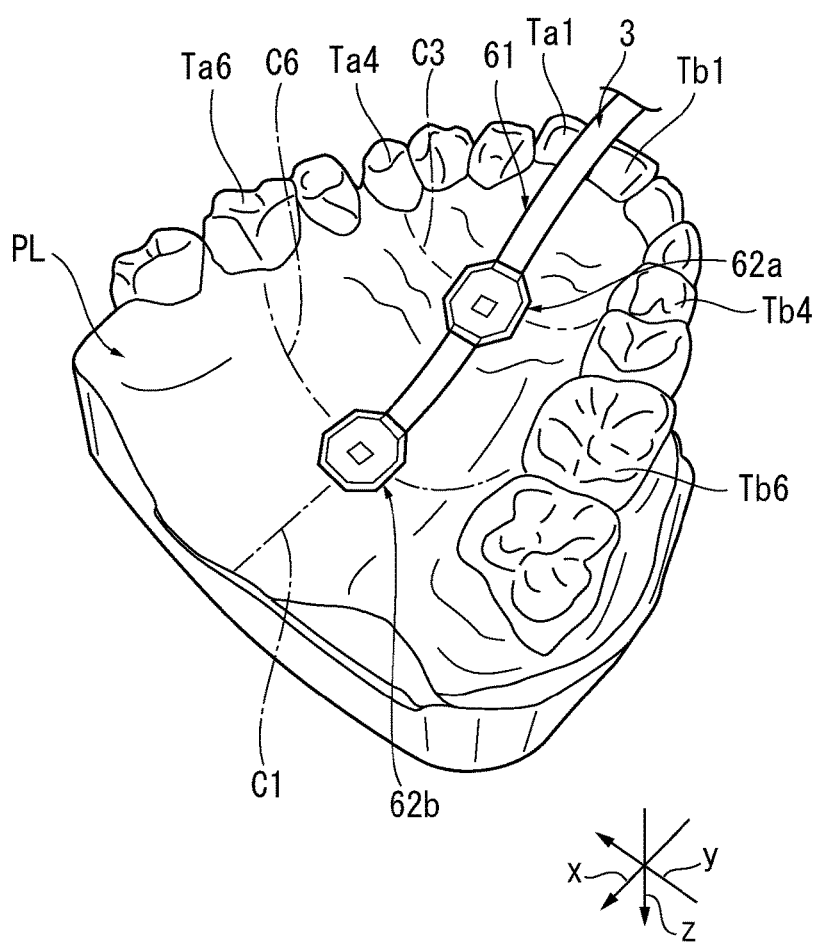
FIG. 22 is a schematic representation showing a state in which an oral cavity sensor according to another embodiment is attached to the palate.
Figure 25:
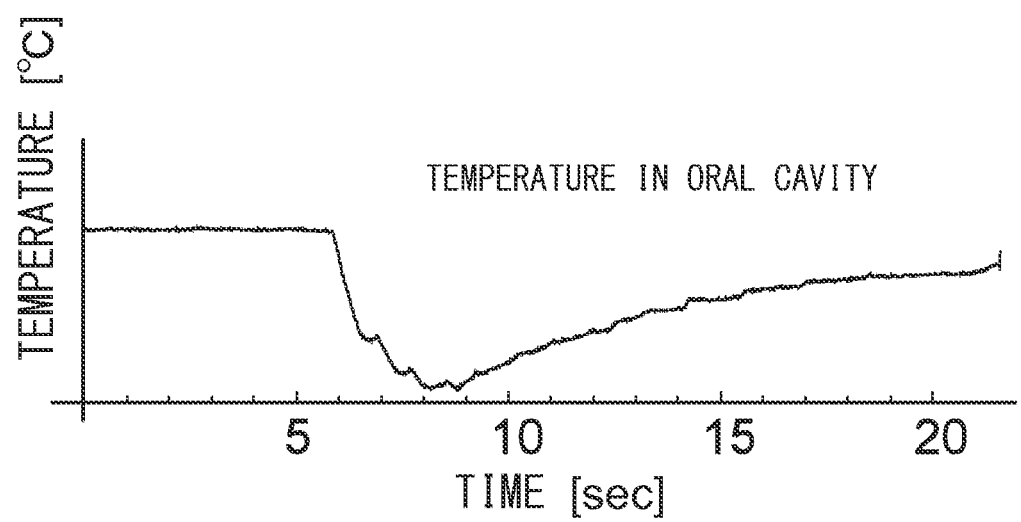
FIG. 25 is a graph showing a temperature change in the oral cavity when an ice cream is swallowed.
Figure 26:
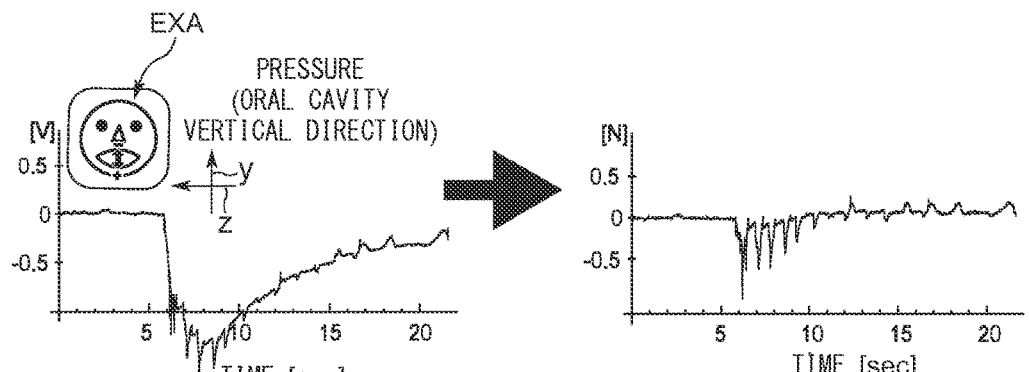
FIG. 26 shows graphs respectively showing measurement results obtained from a first sensor section 21a, a second sensor section 21b, and a third sensor section 21c, and showing results obtained by removing, from the measurement results, temperature dependent resistance value changes.
Figure 26:
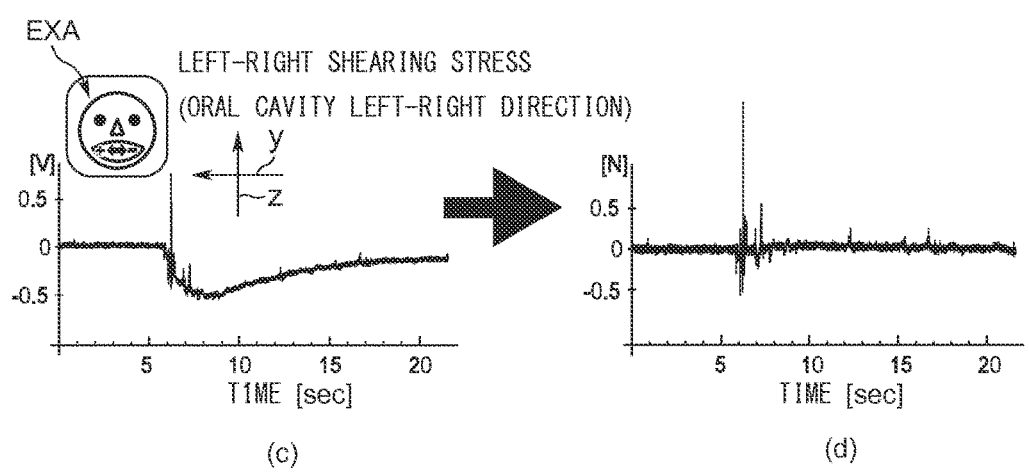
Figure 26:
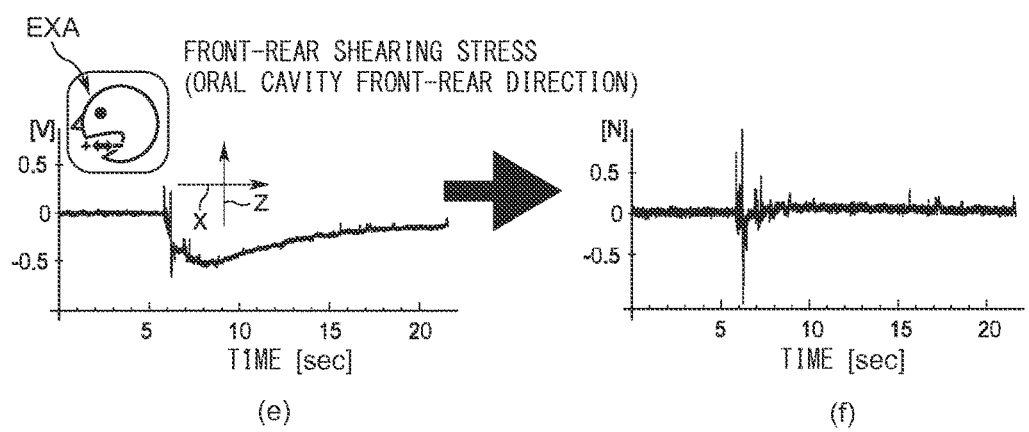

Next, as shown in FIG. 22, the oral cavity sensor 61 was bonded to the palate PL of the subject EXA by a denture stabilizer, and verification tests were performed. FIG. 25 shows a measurement result of the temperature in the oral cavity, the measurement result being obtained on the basis of the measurement result obtained from the temperature sensor section 52 of the second sensor main body 62*b* arranged at the palate PL on the deep side of the oral cavity, and shows a temperature change at the time when the subject EXA swallowed an ice cream after about 6 [SEC] from the start of the measurement. FIG. 26(*a*) shows a measurement result obtained from the third sensor section 21*c* and shows a pressure applied in the oral cavity vertical direction z. Further, FIG. 26 (*c*) shows a measurement result obtained from the second sensor section 21*b* and shows a left-right shearing stress applied in the oral cavity left-right direction y. Further, FIG. 26(*e*) shows a measurement result obtained from the first sensor section 21*a* and shows a front-rear shearing stress applied in the oral cavity front-rear direction x.

The above (*a*), (*c*) and (*e*) of FIG. 26 respectively show measurement results obtained from the second sensor main body 62*b* before performing the temperature correction. From the measurement results, it was confirmed that the measurement results show that each of them also includes the resistance value change generated by the displacement of the piezoresistive layer due to the temperature change. To cope with this, when, in the sensor element 51, the temperature-dependent resistance value change of the piezoresistive layer 29*a* measured by the temperature sensor section 52 was removed from the resistance value changes respectively measured from the first sensor section 21*a*, the second sensor section 21*b*, and the third sensor section 21*c*, the results as shown in (*b*), (*d*) and (*f*) of FIG. 26 were obtained.

In this way, it was confirmed that, in the sensor element 51, the temperature-dependent resistance value change can be removed from each of the measurement results of the first sensor section 21*a*, the second sensor section 21*b*, and the third sensor section 21*c*, and thereby only the resistance value change generated by the external force applied from the tongue TG or fluid F at the time of mastication or swallowing can be measured.

Figure 27:
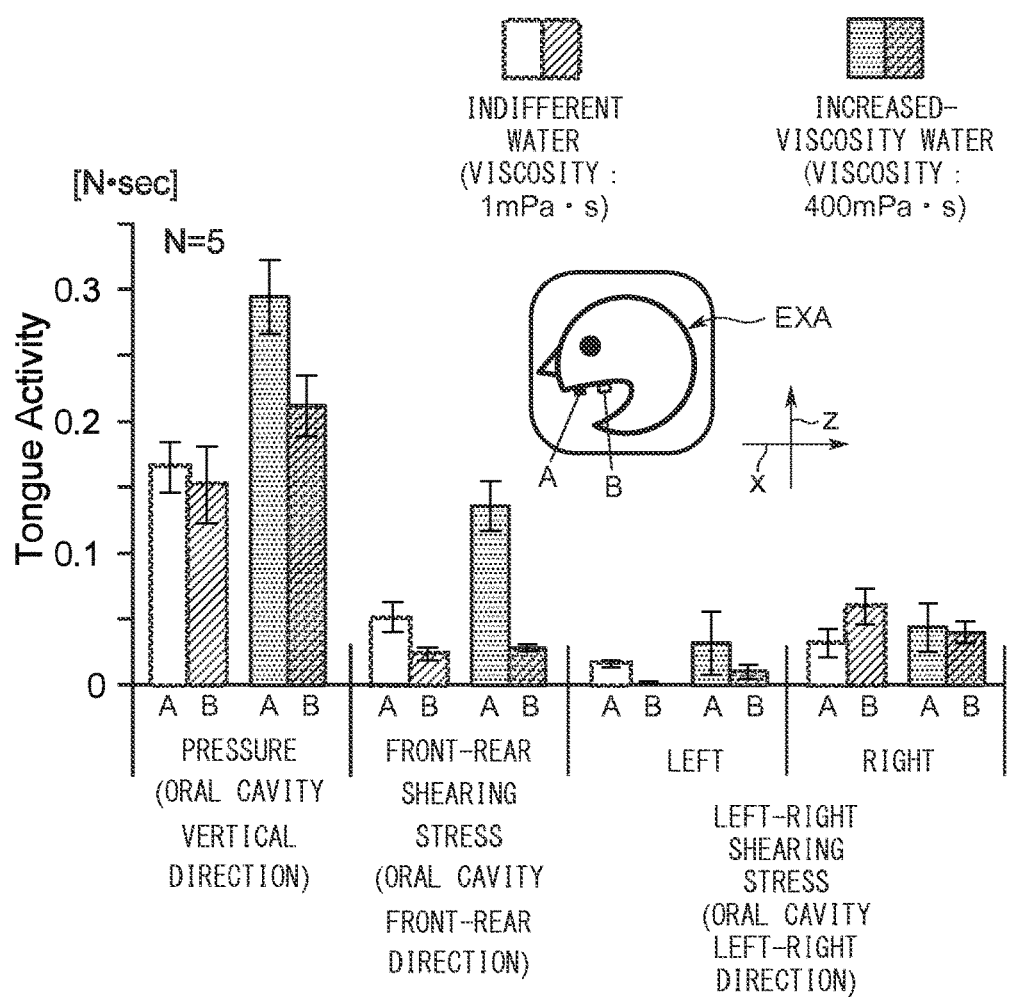
FIG. 27 is a graph showing measurement results obtained respectively from a first sensor main body and a second sensor main body when indifferent water is swallowed and when increased-viscosity water is swallowed.

Next, the subject EXA was made to swallow 15.4 [g] of indifferent water having viscosity of 1 [mPa·s], that is, having almost no viscosity, and 15.4 [g] of increased-viscosity water having a viscosity of 400 [mPa·s] obtained by adding a thickening agent (product name "Toromeiku SP", Meiji Co., Ltd.) into indifferent water. Then, the measurement results obtained by the oral cavity sensor 61 at this time were respectively studied, and the results as shown in FIG. 27 were obtained. It should be noted that, in FIG. 27, the first sensor main body 62*a*, with which the tongue front section TGa comes into contact, is denoted as "A", that the second sensor main body 62*b*, with which the tongue rear section TGb comes into contact, is denoted as "B", and that the time integration of each of measured outputs is defined as tongue activity and denoted as "Tongue Activity" for the vertical axis.

From FIG. 27, it was confirmed that the external force applied by the tongue to the first sensor main body 62*a* on the front side of the palate is relatively larger than the external force applied by the tongue to the second sensor main body 62*b* on the deep side of the palate. Further, it was confirmed that, when increased-viscosity water is swallowed, the tongue activity in each of the oral cavity vertical direction z and the oral cavity front-rear direction x is increased, and the difference in the tongue activity between the tongue front section TGa and the tongue rear section TGb is increased. In this way, with the oral cavity sensor 61, it was possible to analyze the tongue activity in significantly more detail by comparing the activity of the tongue front section TGa with the activity of the tongue rear section TGb.

Figure 28:
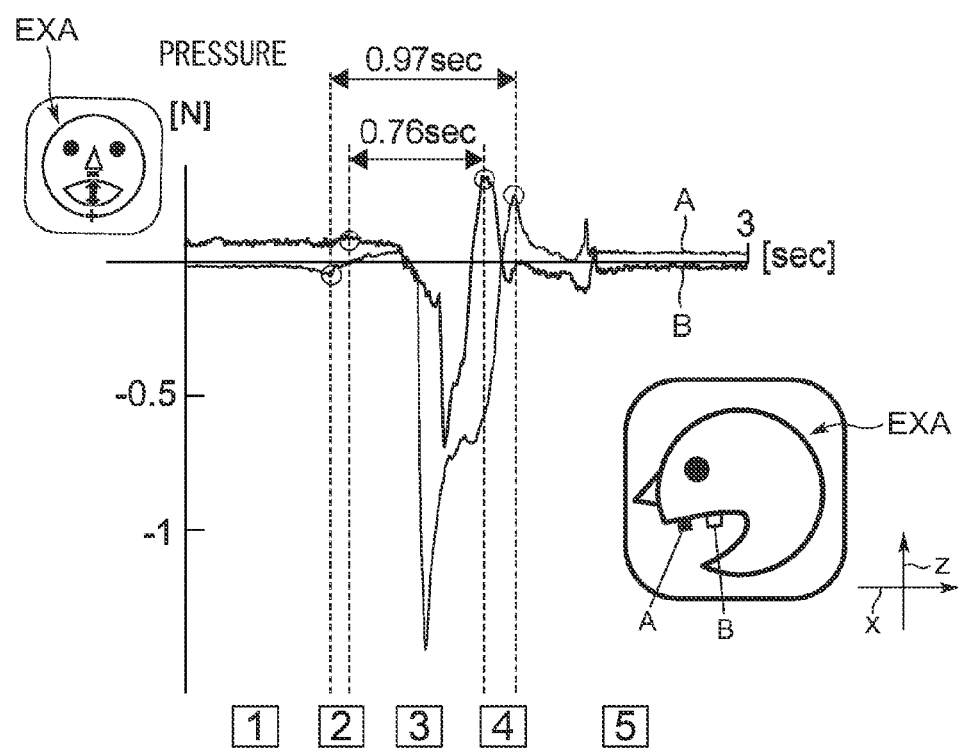
FIG. 28 is a graph showing time-sequential pressure distribution data at the time of swallowing fluid.

FIG. 28 time-sequentially shows measurement results of the pressure applied in the oral cavity vertical direction z, the measurement results being respectively obtained from the first sensor main body 62*a* and the second sensor main body 62*b* which were respectively brought into contact with the tongue front section TGa and the tongue rear section TGb at the time when the subject EXA swallowed fluid F. The movements of the tongue front section TGa and the tongue rear section TGb were analyzed from the pressure distribution data time-sequentially shown in FIG. 28. As a result, it could be inferred that, in the state of "1" in FIG. 28, as shown in FIG. 29A, both of the front section and the rear section of the tongue TG are not in contact with the first sensor main body 62a or the second sensor main body 62b, and the fluid F is placed on the tongue TG.

Figure 29A:
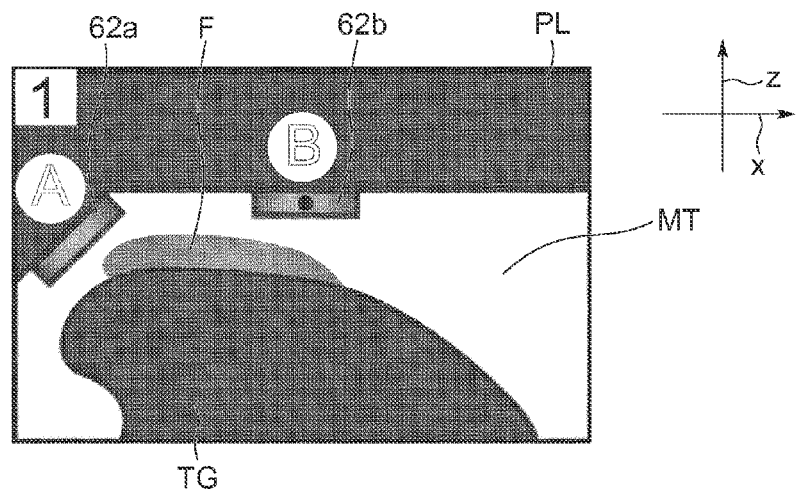
FIG. 29A is a schematic representation showing a state in the oral cavity, which corresponds to the pressure distribution data of "1" shown in FIG. 28.
Figure 29B:
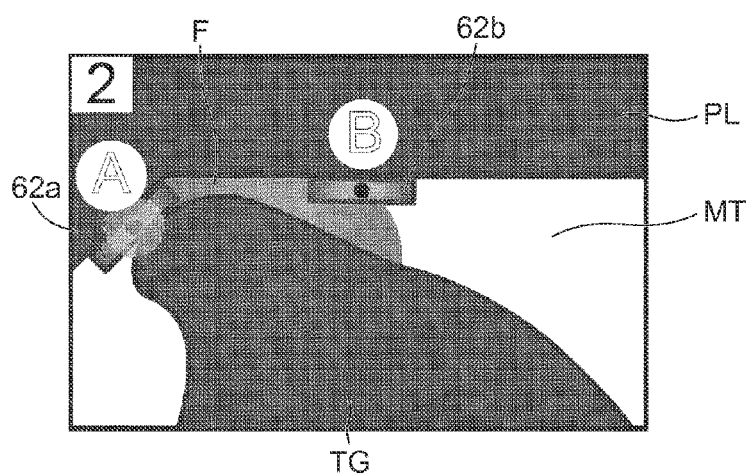
FIG. 29B is a schematic representation showing a state in the oral cavity, which corresponds to the pressure distribution data of "2" shown in FIG. 28.

Further, it could be inferred that, in the state of "2" in FIG. 28, as shown in FIG. 29B, the front section of the tongue TG is in contact with the first sensor main body 62a, and the fluid F is in contact with the second sensor main body 62b. Further, it could be inferred that, in the state of "3" in FIG. 28, as shown in FIG. 29C, the front section of the tongue TG is in contact with the first sensor main body 62a, and also the rear section of the tongue TG is in contact with the second sensor main body 62b, and the fluid F is moved towards the deep side in the oral cavity.

Figure 30A:
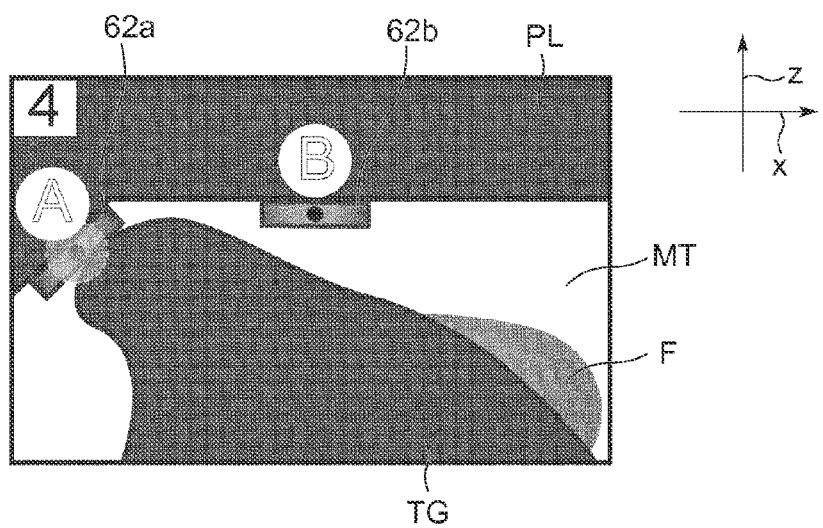
FIG. 30A is a schematic representation showing a state in the oral cavity, which corresponds to the pressure distribution data of "4" shown in FIG. 28.
Figure 30B:
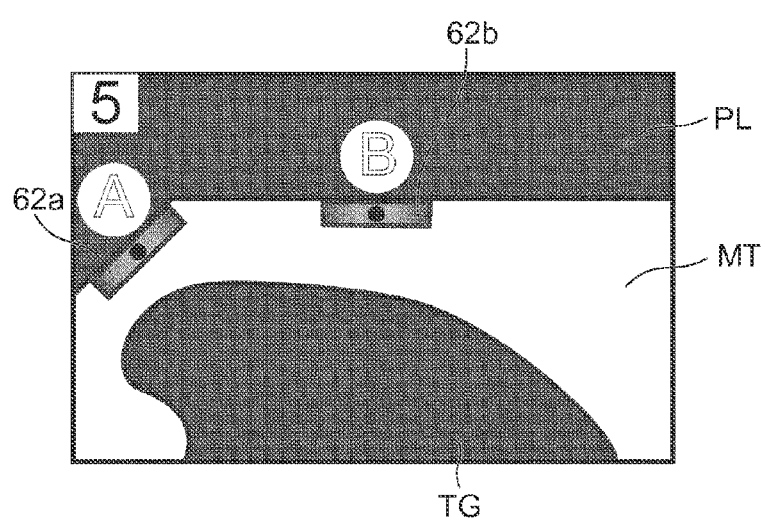
FIG. 30B is a schematic representation showing a state in the oral cavity, which corresponds to the pressure distribution data of "5" shown in FIG. 28.

Further, it could be inferred that, in the state of "4" in FIG. 28, as shown in FIG. 30A, the front section of the tongue TG is in contact with the first sensor main body 62a, but the rear section of the tongue TG is not in contact with the second sensor main body 62b, and then, in the state of "5" in FIG. 28, as shown in FIG. 30B, the tongue TG is not in contact with each of the first sensor main body 62a and the second sensor main body 62b.

Figure 29C:
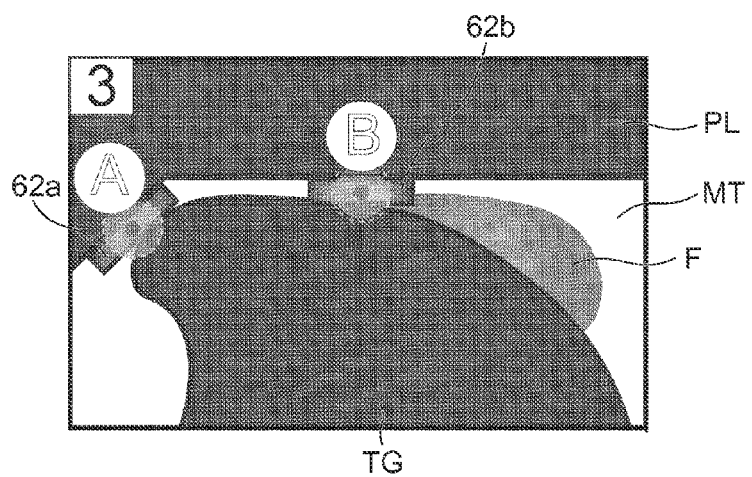
FIG. 29C is a schematic representation showing a state in the oral cavity, which corresponds to the pressure distribution data of "3" shown in FIG. 28.

From the series of tongue movements shown in FIG. 29A to FIG. 29C and in FIG. 30A and FIG. 30B, it was found that, at the time of swallowing the fluid F, the front section of the tongue TG functions as an anchor which closes the inside of the oral cavity so as to prevent the fluid F in the oral cavity from moving to the outside of the oral cavity, and further, the rear section of the tongue TG functions as a pump which transports the fluid F into the esophagus. In this way, with the oral cavity sensor 61, it was possible that the tongue movements were analyzed by being divided into the movements of each of the tongue front section TGa and the tongue rear section TGb, and thereby overall movements of the entire tongue at the time of swallowing could be analyzed in significantly more detail.

In the oral cavity sensor 61 with the above-described configuration, a plurality of sensor main bodies (in this case, the first sensor main body 62a and the second sensor main body 62b) are provided, and the first sensor main body 62a and the second sensor main body 62b are attached in the oral cavity of the subject so that the external force components in the three axis directions were measured from each of the first sensor main body 62a and the second sensor main body 62b. Thereby, in the oral cavity sensor 61, the same effects as those of the first embodiment described above are obtained, and further, external force components in the three axis directions are obtained at each of different positions in the oral cavity, so that complicated tongue movements at the time of mastication or swallowing can be analyzed in more detail than before by comprehensively analyzing the external force components at each of these positions.

Further, in the oral cavity sensor 61 of the present embodiment, the first sensor main body 62a and the second sensor main body 62b are arranged in a row in the oral cavity front-rear direction x so as to respectively come into contact with the tongue front section TGa and the tongue rear section TGb, and thereby complicated tongue movements at the time of mastication or swallowing can be divided into the movements of each of the tongue front section TGa and the tongue rear section TGb, so as to analyze the roles of each of the tongue front section TGa and the tongue rear section TGb.

It should be noted that, in the embodiment described above, a case is described in which the first sensor main body 62a and the second sensor main body 62b are arranged in a row in the oral cavity front-rear direction x so as to respectively come into contact with the tongue front section TGa and the tongue rear section TGb. However, the present invention is not limited to this, and a plurality of the sensor main bodies may be arranged in a row in the oral cavity left-right direction y so as to come into contact with the tongue right side and the tongue left side. Further, a plurality of the sensor main bodies may be arranged in each of the oral cavity left-right direction y and the oral cavity front-rear direction x. For example, when a plurality of the sensor main bodies are provided in the oral cavity left-right direction y, complicated tongue movements at the time of mastication or swallowing can be divided into the movements of each of the tongue right side and the tongue left side, so as to analyze the roles of each of the tongue right side and the tongue left side.

INDUSTRIAL APPLICABILITY

With the oral cavity sensor according to the present invention, it is possible to analyze in detail how the tongue moves, for example, when the subject masticates or swallows food. By using the results of the analysis, it is possible to develop new foods which can be easily swallowed by a dysphagia person, elderly people, and the like, and also it is possible to develop a thickening agent which adds viscosity to food.

The invention claimed is:

1. An oral cavity sensor comprising
a sensor main body configured to be attached in an oral cavity of a subject and configured to measure external force applied from a tongue in the oral cavity,
wherein the sensor main body includes an elastic body elastically deformable by the external force applied from the tongue,
a sensor element embedded in the elastic body and configured, on the basis of a displacement state of the elastic body, to measure external force components in three axis directions orthogonal to each other, said sensor element including a first sensor section deformable in a first direction, a second sensor section deformable in a second direction orthogonal to the first direction, and a third sensor section deformable in a third direction orthogonal to the first direction and the second direction, the first sensor section and the second sensor section each being provided with a cantilever-shape and the third sensor section being provided with a cantilever section having a both-end supported beam, wherein each of the first sensor section, the second sensor section, and the third sensor section includes a piezoresistive layer configured to detect, as a resistance value change, a displacement state thereof, and each of resistance value changes generated in the piezoresistive layers due to movements of the tongue is outputted as an output signal a wiring body and
a coating film made of a para-xylene based polymer and covering the elastic body.

2. The oral cavity sensor according to claim 1, wherein the sensor main body has a configuration in which the sensor element is configured to be attached in the oral cavity of the subject via the elastic body.

3. The oral cavity sensor according to claim 1, wherein the wiring is body configured to be drawn out from the sensor main body and to send out a measurement result obtained by the sensor element to a measurement apparatus,
   wherein the wiring body is also covered with the coating film.

4. The oral cavity sensor according to claim 1, wherein
   the sensor main body is configured to be bonded to a palate in the oral cavity by using, as a bonding surface, the coating film on one side, and the coating film on the other side is used as a contact surface to come into contact with the tongue and is arranged so as to face the tongue, and
   the bonding surface of the sensor main body and the elastic body are displaced by external force applied from the tongue in the oral cavity.

5. The oral cavity sensor according to claim 1, wherein the first sensor section, the second sensor section, and the third sensor section are arranged to satisfy a positional relationship between vertexes of a triangle so as to be adjacent to each other and are collectively arranged at a predetermined position in the oral cavity.

6. The oral cavity sensor according to claim 1, wherein the sensor element includes a temperature sensor section configured not to be deformed by displacement of the elastic body, the temperature sensor section being configured to allow the resistance value thereof to be changed according to a temperature change, and the temperature sensor section sends out, as an output signal, a resistance value change generated due to the temperature change.

\* \* \* \* \*

UNITED STATES PATENT AND TRADEMARK OFFICE
CERTIFICATE OF CORRECTION

PATENT NO. : 9,504,417 B2
APPLICATION NO. : 14/363361
DATED : November 29, 2016
INVENTOR(S) : Isao Shimoyama et al.

Page 1 of 1

It is certified that error appears in the above-identified patent and that said Letters Patent is hereby corrected as shown below:

In the Specification

Column 21, Line 2; please delete "Ta1" and add -- Ta7 --

Column 21, Line 7; please delete "Ta1" and add -- Ta7 --

Signed and Sealed this
Eighteenth Day of April, 2017

Michelle K. Lee
*Director of the United States Patent and Trademark Office*